(12) United States Patent
Goulet et al.

(10) Patent No.: US 7,622,449 B2
(45) Date of Patent: Nov. 24, 2009

(54) ANTI-HYPERCHOLESTEROLEMIC COMPOUNDS

(75) Inventors: Mark T. Goulet, Lexington, MA (US); Feroze Ujjainwalla, Scotch Plains, NJ (US); Anthony Ogawa, Mountainside, NJ (US); Derek Von Langen, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 556 days.

(21) Appl. No.: 11/153,192

(22) Filed: Jun. 15, 2005

(65) Prior Publication Data

US 2005/0267049 A1    Dec. 1, 2005

Related U.S. Application Data

(63) Continuation-in-part of application No. PCT/US2004/042698, filed on Dec. 17, 2004.

(60) Provisional application No. 60/532,096, filed on Dec. 23, 2003.

(51) Int. Cl.
*C07H 15/203* (2006.01)
*C07H 15/26* (2006.01)
*A61P 9/10* (2006.01)
*A61P 3/06* (2006.01)
*A61K 31/7052* (2006.01)
*C07D 205/08* (2006.01)
*A61K 31/397* (2006.01)

(52) U.S. Cl. .................. 514/25; 536/17.4; 540/200; 514/32

(58) Field of Classification Search .................. None
See application file for complete search history.

(56) References Cited

U.S. PATENT DOCUMENTS

| | | | |
|---|---|---|---|
| 5,306,817 A | 4/1994 | Thiruvengadam et al. | |
| 5,561,227 A | 10/1996 | Thiruvengadam et al. | |
| 5,624,920 A | 4/1997 | McKittrick et al. | |
| 5,627,176 A | 5/1997 | Kirkup et al. | |
| 5,631,365 A | 5/1997 | Rosenblum et al. | |
| 5,633,246 A | 5/1997 | McKittrick et al. | |
| 5,656,624 A | 8/1997 | Vaccaro et al. | |
| 5,661,145 A | 8/1997 | Davis | |
| 5,688,785 A | 11/1997 | Vaccaro | |
| 5,688,787 A | 11/1997 | Burnett et al. | |
| 5,688,990 A | 11/1997 | Shankar | |
| 5,728,827 A | 3/1998 | Thiruvengadam et al. | |
| 5,744,467 A | 4/1998 | McKittrick et al. | |
| 5,756,470 A | 5/1998 | Yumibe et al. | |
| 5,767,115 A | 6/1998 | Rosenlum et al. | |
| 5,846,966 A | 12/1998 | Rosenblum et al. | |
| RE37,721 E | 5/2002 | Rosenblum et al. | |
| 6,632,933 B2 | 10/2003 | Altmann et al. | |
| 2002/0039774 A1 | 4/2002 | Kramer et al. | |
| 2002/0137690 A1 | 9/2002 | Ghosal et al. | |
| 2005/0239766 A1* | 10/2005 | Starke et al. | 514/210.02 |
| 2005/0267038 A1* | 12/2005 | Glombik et al. | 514/16 |
| 2006/0135755 A1* | 6/2006 | Thiruvengadam et al. | 536/17.4 |
| 2007/0078098 A1* | 4/2007 | DeVita et al. | 514/23 |
| 2007/0149776 A1* | 6/2007 | Lindenschmidt et al. | 540/200 |
| 2007/0155676 A1* | 7/2007 | Burnett et al. | 514/23 |
| 2008/0280836 A1 | 11/2008 | Morriello et al. | |

FOREIGN PATENT DOCUMENTS

| | | |
|---|---|---|
| WO | WO00/63703 | 10/2000 |
| WO | WO2005/044256 | 5/2005 |
| WO | 2005/069900 A2 | 8/2005 |
| WO | WO2006086562 A * | 8/2006 |
| WO | WO2006/138163 | 12/2006 |
| WO | 2008/057336 A1 | 7/2008 |
| WO | 2008/085300 A1 | 7/2008 |

OTHER PUBLICATIONS

Burnett, Duane A. et al., Bioorganic & Medicinal Chemistry Letters, vol. 12(3), pp. 315-318, 2002.
U.S. Appl. No. 60/537,341 Publication Date - Aug. 4, 2005 - Garcia-Calvo (see attachment for details regarding online publication).

* cited by examiner

*Primary Examiner*—Mark L Berch
(74) *Attorney, Agent, or Firm*—Carol S. Quagliato; Mark R. Daniel

(57) ABSTRACT

This invention provides cholesterol absorption inhibitors of Formula I:

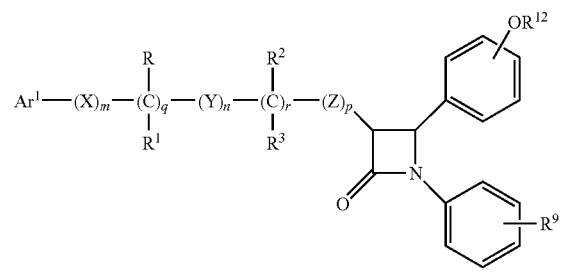

and the pharmaceutically acceptable salts and esters thereof. The compounds are useful for lowering plasma cholesterol levels, particularly LDL cholesterol, and for treating and preventing atherosclerosis and atherosclerotic disease events.

29 Claims, No Drawings

ANTI-HYPERCHOLESTEROLEMIC COMPOUNDS

RELATED APPLICATIONS

This application is a continuation-in-part of International Application No. PCT/US2004/042698, filed Dec. 17, 2004, which claims the benefit under 35 U.S.C. §119(e) of U.S. Provisional Application No. 60/532096, filed Dec. 23, 2003.

BACKGROUND OF THE INVENTION

The instant invention relates to substituted 2-azetidinones and the pharmaceutically acceptable salts and esters thereof, and to their use alone or in combination with other active agents to treat hypercholesterolemia and for preventing, halting or slowing the progression of atherosclerosis and related conditions and disease events.

It has been clear for several decades that elevated blood cholesterol is a major risk factor for coronary heart disease, and many studies have shown that the risk of CHD events can be reduced by lipid-lowering therapy. Prior to 1987, the lipid-lowering armamentarium was limited essentially to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. Substantial reductions in LDL (low density lipoprotein) cholesterol accompanied by increases in HDL (high density lipoprotein) cholesterol could be achieved by the combination of a lipid-lowering diet and a bile acid sequestrant, with or without the addition of nicotinic acid. However, this therapy is not easy to administer or tolerate and was therefore often unsuccessful except in specialist lipid clinics. The fibrates produce a moderate reduction in LDL cholesterol accompanied by increased HDL cholesterol and a substantial reduction in triglycerides, and because they are well tolerated these drugs have been more widely used. Probucol produces only a small reduction in LDL cholesterol and also reduces HDL cholesterol, which, because of the strong inverse relationship between HDL cholesterol level and CHD risk, is generally considered undesirable. With the introduction of lovastatin, the first inhibitor of HMG-CoA reductase to become available for prescription in 1987, for the first time physicians were able to obtain large reductions in plasma cholesterol with very few adverse effects.

Recent studies have unequivocally demonstrated that lovastatin, simvastatin and pravastatin, all members of the HMG-CoA reductase inhibitor class, slow the progression of atherosclerotic lesions in the coronary and carotid arteries. Simvastatin and pravastatin have also been shown to reduce the risk of coronary heart disease events, and in the case of simvastatin a highly significant reduction in the risk of coronary death and total mortality has been shown by the Scandinavian Simvastatin Survival Study. This study also provided some evidence for a reduction in cerebrovascular events. Despite the substantial reduction in the risk of coronary morbidity and mortality achieved by simvastatin, the risk is still substantial in the treated patients. For example, in the Scandinavian Simvastatin Survival Study, the 42% reduction in the risk of coronary death still left 5% of the treated patients to die of their disease over the course of this 5 year study. Further reduction of risk is clearly needed.

A more recent class of anti-hyperlipidemic agents that has emerged includes inhibitors of cholesterol absorption. Ezetimibe, the first compound to receive regulatory approval in this class, is currently marketed in the U.S. under the tradename ZETIA®. Ezetimibe has the following chemical structure and is described in U.S. Pat. Nos. Re. 37721 and 5,846,966:

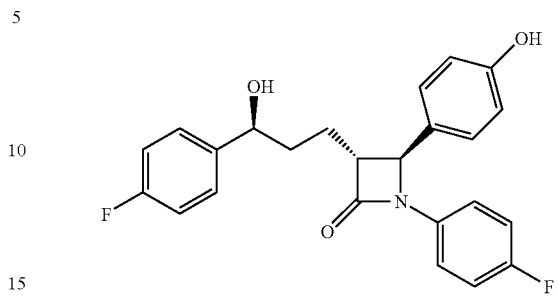

Sugar-substituted 2-azetidinones, including glucuronidated analogs of the following general structure:

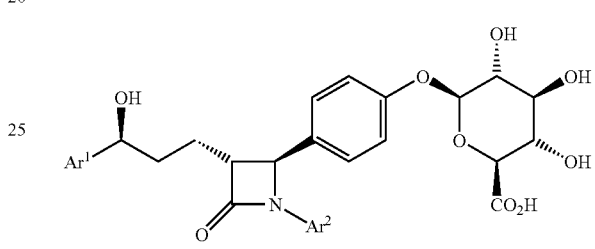

and methods for making them are disclosed in U.S. Pat. No. 5,756,470, wherein $Ar^1$ and $Ar^2$ are unsubstituted or substituted aryl groups.

Additional cholesterol absorption inhibitors are described in WO2002/066464 A1 (applied for by Kotobuki Pharmaceutical Co.), and U.S. 2002/0137689 A1 (Glombik et al.). WO2002/066464 A1 discloses hypolipidemic compounds of general formula

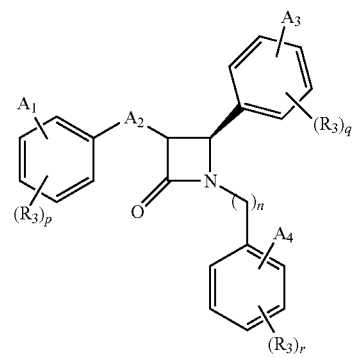

wherein, among other definitions, $A_1$, $A_3$ and $A_4$ can be

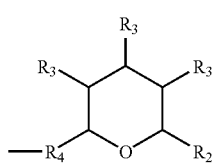

and wherein $R_2$ is —$CH_2OH$, —$CH_2OC(O)$—$R_1$, or —$CO_2R_1$; $R_3$ is —OH or —$OC(O)R_1$, and $R_4$ is —$(CH_2)_kR_5(CH_2)_i$— where k and i are zero or integers of one or more, and k+i is an integer of 10 or less; and $R_5$ is a single bond, —CH=CH—, —$OCH_2$—, carbonyl or —CH(OH).

U.S. 2002/0137689 A1 discloses hypolipidemic compounds of general formula

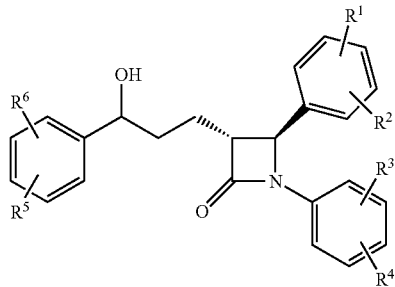

wherein, among other definitions, $R^1$, $R^2$, $R^3$, $R^4$, $R^5$, $R^6$ independently of one another can be $(C_0-C_{30})$-alkylene-(LAG), where one or more carbon atoms of the alkylene radical may be replaced by —O—, —(C=O)—, —CH=CH—, —C≡C—, —$N((C_1-C_6)$-alkyl)-, —$N((C_1-C_6)$-alkylphenyl) or —NH—; and (LAG) is a sugar residue, disugar residue, trisugar residue, tetrasugar residue; a sugar acid, or an amino sugar.

In the ongoing effort to discover novel treatments for hyperlipidemia and atherosclerotic process, the instant invention provides novel cholesterol absorption inhibitors, described below.

SUMMARY OF THE INVENTION

One object of the instant invention provides novel cholesterol absorption inhibitors of Formula I

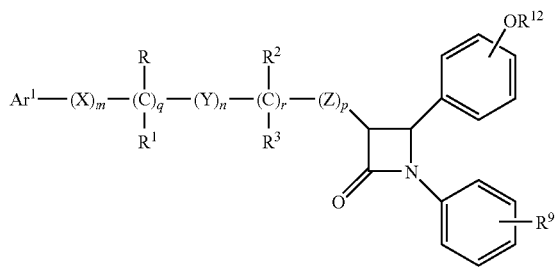

and the pharmaceutically acceptable salts and esters thereof.

A second object of the instant invention is to provide a method for inhibiting cholesterol absorption comprising administering a therapeutically effective amount of a compound of Formula I to a patient in need of such treatment. Another object is to provide a method for reducing plasma cholesterol levels, especially LDL-cholesterol, and treating hypercholesterolemia comprising administering a therapeutically effective amount of a compound of Formula I to a patient in need of such treatment.

As a further object, methods are provided for preventing or reducing the risk of developing atherosclerosis, as well as for halting or slowing the progression of atherosclerotic disease once it has become clinically evident, comprising the administration of a prophylactically or therapeutically effective amount, as appropriate, of a compound of Formula I to a patient who is at risk of developing atherosclerosis or who already has atherosclerotic disease. Another object of the present invention is the use of the compounds of the present invention for the manufacture of a medicament useful in treating, preventing or reducing the risk of developing these conditions. Other objects of this invention are to provide processes for making the compounds of Formula I and to provide novel pharmaceutical compositions comprising these compounds.

Additionally the compounds of this invention, particularly radioactive isotopes of the compounds of Formula I, can be used in screening assays, where the assay is designed to identify new cholesterol absorption inhibitors that have the same mechanism of action as ezetimibe. Additional objects will be evident from the following detailed description.

DETAILED DESCRIPTION OF THE INVENTION

The novel cholesterol absorption inhibitors of the instant invention are compounds of Formula I

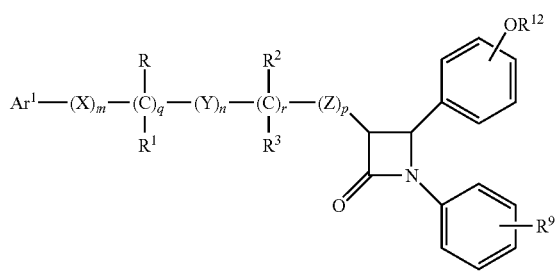

and the pharmaceutically acceptable salts and esters thereof, wherein $Ar^1$ is selected from the group consisting of aryl and $R^4$-substituted aryl;

X, Y and Z are independently selected from the group consisting of —$CH_2$—, —$CH(C_{1-6}alkyl)$- and —$C(C_{1-6}alkyl)_2$—;

R is selected from the group consisting of —$OR^6$, —$O(CO)R^6$, —$O(CO)OR^8$, —$O(CO)OR^9$, —$O(CO)NR^6R^7$, a sugar residue, a disugar residue, a trisugar residue and a tetrasugar residue;

$R^1$ is selected from the group consisting of —H, —$C_{1-6}alkyl$ and aryl, or R and $R^1$ together are oxo;

$R^2$ is selected from the group consisting of —$OR^6$, —$O(CO)R^6$, —$O(CO)OR^8$, —$O(CO)OR^9$ and —$O(CO)NR^6R^7$;

$R^3$ is selected from the group consisting of —H, —$C_{1-6}alkyl$ and aryl or $R^2$ and $R^3$ together are oxo;

q and r are integers each independently selected from 0 and 1;

t is an integer selected from 0, 1 and 2;

m, n and p are integers each independently selected from 0, 1, 2, 3 and 4;

$R^4$ is 1-5 substituents independently selected at each occurrence from the group consisting of: —$OR^5$, —$O(CO)R^5$, —$O(CO)OR^8$, —$O$—$C_{1-5}alkyl$-$OR^5$, —$O(CO)NR^5R^6$, —$NR^5R^6$, —$NR^5(CO)R^6$, —$NR^5(CO)OR^8$, —$NR^5(CO)NR^6R^7$, —$NR^5SO_2R^8$, —$COOR^5$, —$CONR^5R^6$, —$COR^5$, —$SO_2NR^5R^6$, —$S(O)_tR^8$, —O—$C_{1-10}alkyl$-$COOR^5$, —O—$C_{1-10}alkyl$-$CONR^5R^6$ and fluoro;

$R^5$, $R^6$ and $R^7$ are independently selected at each occurrence from the group consisting of —H, $C_{1-6}alkyl$, aryl and aryl-substituted $C_{1-6}alkyl$;

$R^8$ is independently selected from the group consisting of $C_{1-6}$alkyl, aryl and aryl-substituted $C_{1-6}$alkyl;

$R^9$ is selected from the group consisting of —C≡C—CH$_2$—NR$^{10}$R$^{11}$, —C≡C—C(O)R$^{13}$, and —(CH$_2$)$_3$—NR$^{10}$R$^{14}$;

$R^{10}$ is independently selected at each occurrence from —H and —C$_{1-3}$alkyl;

$R^{11}$ is selected from the group consisting of —H, —C$_{1-3}$alkyl, —C(O)—C$_{1-3}$alkyl, —C(O)—NR$^{10}$R$^{10}$, —SO$_2$—C$_{1-3}$alkyl, and —SO$_2$-phenyl; and $R^{12}$ is selected from —H,

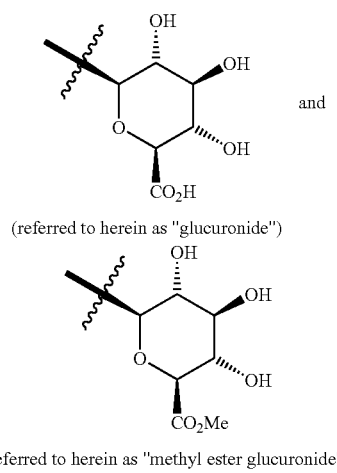

(referred to herein as "glucuronide")

(referred to herein as "methyl ester glucuronide");

$R^{13}$ is selected from the group consisting of —OH and —NR$^{10}$R$^{11}$; and $R^{14}$ is selected from the group consisting of —C(O)—C$_{1-3}$alkyl, —C(O)—NR$^{10}$R$^{10}$, —SO$_2$—C$_{1-3}$alkyl and —SO$_2$-phenyl.

In one embodiment of this invention are compounds of Formula I wherein at least one of q and r is 1, and the sum of m, n, p, q and r is 1, 2, 3, 4, 5 or 6. In a class of this embodiment are compounds wherein the sum of m, q and n is 1, 2, 3, 4, or 5 when p is 0 and r is 1.

In another embodiment of this invention are compounds of Formula I wherein: R is selected from the group consisting of —OR$^6$, —O(CO)R$^6$, —O(CO)OR$^9$, —O(CO)NR$^6$R$^7$, a sugar residue, a disugar residue, a trisugar residue and a tetrasugar residue; $R^2$ is selected from the group consisting of —OR$^6$, —O(CO)R$^6$, —O(CO)OR$^9$ and —O(CO)NR$^6$R$^7$; and t is selected from 0 and 1. In a class of this embodiment are compounds wherein q, r and t are each independently selected from 0 and 1; and m, n and p are each independently selected from 0, 1, 2, 3 and 4; provided that at least one of q and r is 1, and the sum of m, n, p, q and r is 1, 2, 3, 4, 5 or 6; and provided that when p is 0 and r is 1, the sum of m, q and n is 1, 2, 3, 4, or 5.

In another embodiment of this invention are compounds of Formula I wherein R is selected from the group consisting of —OR$^6$, —O(CO)R$^6$, —O(CO)OR$^8$, —O(CO)NR$^6$R$^7$, a sugar residue, a disugar residue, a trisugar residue and a tetrasugar residue; and $R^2$ is selected from the group consisting of —OR$^6$, —O(CO)R$^6$, —O(CO)R$^8$ and —O(CO)NR$^6$R$^7$. In a class of this embodiment are compounds wherein m, n and p are each independently selected from 0, 1, 2, 3 and 4, provided that at least one of q and r is 1, and the sum of m, n, p, q and r is 1, 2, 3, 4, 5 or 6. In a sub-class of this class are compounds wherein the sum of m, q and n is 1, 2, 3, 4, or 5 when p is 0 and r is 1.

In another embodiment of this invention are compounds Formula I having Formula Ia,

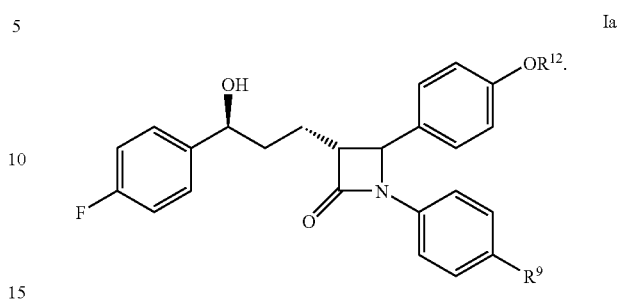

In a further class of each of these embodiments, classes and subclasses are compounds wherein $R^9$ is —C≡C—CH$_2$—NR$^{10}$R$^{11}$.

As used herein "alkyl" is intended to include both branched- and straight-chain saturated aliphatic univalent hydrocarbon groups having the specified number of carbon atoms. Examples of alkyl groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tertbutyl (t-Bu), isopentyl, isohexyl and the like. If there is no specified prefix (such as "n-" for normal, "s-" for sec, "t-" for tert, "i-" for iso) with a named alkyl group, then it is intended that the named alkyl goup is an n-alkyl group (i.e., "propyl" is "n-propyl"). As used herein within the definitions of variable groups in Formula I, "alkyl" may also be divalent, as for example when $R^8$ is aryl-substituted —$C_{1-6}$ alkyl or when $R^4$ is —OC$_{1-10}$alkyl-COOR$^5$.

As used herein, "aryl" is intended to include phenyl (Ph), naphthyl, indenyl, tetrahydronaphthyl or indanyl. Phenyl is preferred.

Suitable protecting groups (designated as "PG" herein) for the hydroxyl groups of $R^{12}$ when $R^{12}$ is a glucuronide or methyl ester glucuronide include but are not limited to those that are known to be useful as carbohydrate protecting groups, such as for example benzyl, acetyl, benzoyl, tert-butyldiphenylsilyl, trimethylsilyl, para-methoxybenzyl, benzylidine, and methoxy methyl. Conditions required to selectively add and remove such protecting groups are found in standard textbooks such as Greene, T, and Wuts, P. G. M., *Protective Groups in Organic Synthesis*, John Wiley & Sons, Inc., New York, N.Y., 1999.

Compounds of Formula I may contain one or more asymmetric centers and can thus occur as racemates and racemic mixtures, single enantiomers, enantiomeric mixtures, diastereomeric mixtures and individual diastereomers. The present invention is meant to comprehend all such isomeric forms of the compounds of Formula I. All such isomeric forms of the compounds of Formula I are included within the scope of this invention. Furthermore, some of the crystalline forms for compounds of the present invention may exist as polymorphs and as such are intended to be included in the present invention. In addition, some of the compounds of the instant invention may form solvates with water or organic solvents. Such hydrates and solvates are also encompassed within the scope of this invention.

Due to their activity as cholesterol absorption inhibitors, the compounds of the present invention can be used in screening assays, where the assay is designed to identify new cholesterol absorption inhibitors. Radioactive isotopes of the compounds of Formula I are particularly useful in such assays, for example compounds of Formula I wherein sulfur is replaced with "hot" —$^{35}$S—, and particularly wherein the radioactive sulfur isotope is incorporated within the $R^9$ moiety. All such radioactive isotopes of the compounds of Formula I are included within the scope of this invention.

Herein, the term "pharmaceutically acceptable salts" shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, morpholine, 2,4,4-trimethyl-2-pentamine and tris(hydroxymethyl)aminomethane.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Examples of pharmaceutically acceptable esters include, but are not limited to, —$C_{1-4}$alkyl and —$C_{1-4}$ alkyl substituted with phenyl, dimethylamino and acetylamino. "$C_{1-4}$ alkyl" herein includes straight or branched aliphatic chains containing from 1 to 4 carbon atoms, for example methyl, ethyl, n-propyl, n-butyl, iso-propyl, sec-butyl and tert-butyl.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk for diseases and medical conditions affected by inhibition of cholesterol absorption.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. Particularly, the dosage a patient receives can be selected so as to achieve the amount of LDL cholesterol lowering desired; the dosage a patient receives may also be titrated over time in order to reach a target LDL level. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition.

The compounds of the instant invention are cholesterol absorption inhibitors and are useful for reducing plasma cholesterol levels, particularly reducing plasma LDL cholesterol levels, when used either alone or in combination with another active agent, such as an anti-atherosclerotic agent, and more particularly a cholesterol biosynthesis inhibitor, for example an HMG-CoA reductase inhibitor. Thus the instant invention provides methods for inhibiting cholesterol absorption and for treating lipid disorders including hypercholesterolemia, comprising administering a therapeutically effective amount of a compound of Formula I to a person in need of such treatment. Further provided are methods for preventing or reducing the risk of developing atherosclerosis, as well as for halting or slowing the progression of atherosclerotic disease once it has become clinically evident, comprising the administration of a prophylactically or therapeutically effective amount, as appropriate, of a compound of Formula I to a mammal who is at risk of developing atherosclerosis or who already has atherosclerotic disease.

Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction are all clinical manifestations of atherosclerosis and are therefore encompassed by the terms "atherosclerosis" and "atherosclerotic disease."

A compound of Formula I may be administered to prevent or reduce the risk of occurrence, or recurrence where the potential exists, of a coronary heart disease event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a compound of Formula I to a patient at risk for such an event. The patient may or may not have atherosclerotic disease at the time of administration, or may be at risk for developing it.

Persons to be treated with the instant therapy include those at risk of developing atherosclerotic disease and of having an atherosclerotic disease event. Standard atherosclerotic disease risk factors are known to the average physician practicing in the relevant fields of medicine. Such known risk factors include but are not limited to hypertension, smoking, diabetes, low levels of high density lipoprotein (HDL) cholesterol, and a family history of atherosclerotic cardiovascular disease. Published guidelines for determining those who are at risk of developing atherosclerotic disease can be found in: Executive Summary of the Third Report of the National Cholesterol Education Program (NCEP) Expert Panel on Detection, Evaluation, and Treatment of High Blood Cholesterol in Adults (Adult Treatment Panel E), JAMA, 2001; 285 pp. 2486-2497. People who are identified as having one or more of the above-noted risk factors are intended to be included in the group of people considered at risk for developing atherosclerotic disease. People identified as having one or more of the above-noted risk factors, as well as people who already have atherosclerosis, are intended to be included within the group of people considered to be at risk for having an atherosclerotic disease event.

The oral dosage amount of the compound of Formula I, is from about 0.1 to about 30 mg/kg of body weight per day, preferably about 0.1 to about 15 mg/kg of body weight per day. For an average body weight of 70 kg, the dosage level is therefore from about 5 mg to about 1000 mg of drug per day. However, dosage amounts will vary depending on factors as noted above, including the potency of the particular compound. Although the active drug of the present invention may be administered in divided doses, for example from two to four times daily, a single daily dose of the active drug is preferred. As examples, the daily dosage amount may be selected from, but not limited to, 5 mg, 10 mg, 15 mg, 20 mg, 25 mg, 40 mg, 50 mg, 75 mg, 80 mg, 100 mg and 200 mg.

The active drug employed in the instant therapy can be administered in such oral forms as tablets, capsules, pills, powders, granules, elixirs, tinctures, suspensions, syrups, and emulsions. Oral formulations are preferred.

For compounds of Formula I, administration of the active drug can be via any pharmaceutically acceptable route and in any pharmaceutically acceptable dosage form. This includes the use of oral conventional rapid-release, time controlled-release and delayed-release (such enteric coated) pharmaceutical dosage forms. Additional suitable pharmaceutical compositions for use with the present invention are known to those of ordinary skill in the pharmaceutical arts; for example, see Remington's Pharmaceutical Sciences, Mack Publishing Co., Easton, Pa.

In the methods of the present invention, the active drug is typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with a non-toxic, pharmaceutically acceptable, inert carrier such as lactose, starch, sucrose, glucose, modified sugars, modified starches, methyl cellulose and its derivatives, dicalcium phosphate, calcium sulfate, mannitol, sorbitol and other reducing and non-reducing sugars, magnesium stearate, steric acid, sodium stearyl fumarate, glyceryl behenate, calcium stearate and the like. For oral administration in liquid form, the drug components can be combined with non-toxic, pharmaceutically acceptable inert carrier such as ethanol, glycerol, water and the like. Moreover, when desired or necessary, suitable binders, lubricants, disintegrating agents and coloring and flavoring agents can also be incorporated into the mixture. Stabilizing agents such as antioxidants, for example butylated hydroxyanisole (BHA), 2,6-di-tert-butyl-4-methylphenol (BHT), propyl gallate, sodium ascorbate, citric acid, calcium metabisulphite, hydroquinone, and 7-hydroxycoumarin, particularly BHA, propyl gallate and combinations thereof, can also be added to stabilize the dosage forms. When a compound of Formula I is formulated together with an HMG-CoA reductase inhibitor such as simvastatin, the use of at least one stabilizing agent is preferred in the composition. Other suitable components include gelatin, sweeteners, natural and synthetic gums such as acacia, tragacanth or alginates, carboxymethylcellulose, polyethylene glycol, waxes and the like.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipatic block copolymers of hydrogels.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier.

One or more additional active agents may be administered in combination with a compound of Formula I, and therefore an embodiment of the instant invention encompasses a drug combination. The drug combination encompasses a single dosage formulation comprised of the compound of Formula I and additional active agent or agents, as well as administration of each of the compound of Formula I and the additional active agent or agents in separate dosage formulations, which allows for concurrent or sequential administration of the active agents. The additional active agent or agents can be lipid modifying agents, particularly a cholesterol biosynthesis inhibitor, or agents having other pharmaceutical activities, or agents that have both lipid-modifying effects and other pharmaceutical activities. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (see U.S. Pat. No. 4,342,767), simvastatin (see U.S. Pat. No. 4,444,784), dihydroxy open-acid simvastatin, particularly the ammonium or calcium salts thereof, pravastatin, particularly the sodium salt thereof (see U.S. Pat. No. 4,346,227), fluvastatin, particularly the sodium salt thereof (see U.S. Pat. No. 5,354,772), atorvastatin, particularly the calcium salt thereof (see U.S. Pat. No. 5,273,995), pitavastatin also referred to as NK-104 (see PCT international publication number WO 97/23200) and rosuvastatin, (CRESTOR®; see U.S. Pat. No. 5,260,440, and *Drugs of the Future*, 1999, 24(5), pp. 511-513); HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol;

niacin; cholesterol absorption inhibitors such as SCH-58235, which is described in U.S. Pat. Nos. 5,767,115 and 5,846,966; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example troglitazone, pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABC1 gene expression; FXR ligands including both inhibitors and agonists; and LXR ligands including both inhibitors and agonists of all subtypes of this receptor, e.g., LXRα and LXRβ; bisphosphonate compounds such as alendronate sodium; and cyclooxygenase-2 inhibitors such as rofecoxib and celecoxib. Additionally, the compound of Formula Is of this invention, for example compound I, may be used in combination with anti-retroviral therapy in ADDS infected patients to treat lipid abnormalities associated with such treatment, for example but not limited to their use in combination with HIV protease inhibitors such as indinavir, nelfinavir, ritonavir and saquinavir.

A therapeutically or prophylactically effective amount, as appropriate, of a compound of Formula I can be used for the preparation of a medicament useful for inhibiting cholesterol absorption, as well as for treating and/or reducing the risk for diseases and conditions affected by inhibition of cholesterol absorption, such as treating lipid disorders, preventing or reducing the risk of developing atherosclerotic disease, halting or slowing the progression of atherosclerotic disease once it has become clinically manifest, and preventing or reducing the risk of a first or subsequent occurrence of an atherosclerotic disease event. For example, the medicament may be comprised of about 5 mg to about 1000 mg of a compound of Formula I. The medicament comprised of a compound of Formula I may also be prepared with one or more additional active agents, such as those described supra.

The compounds of this invention inhibit cholesterol absorption as exemplified by the following. Compound 7b (shown in Example 7) was tested for inhibition of cholesterol absorption in mice, and its activity was compared to that of ezetimibe. C57BL/6 male mice (n=6/group), aged 7-8 weeks, were dosed orally with 0.1 ml 0.25% methyl cellulose solution with or without test compound, ezetimibe or 7b (0.12-10 mg/kg). Thirty minutes later all of the mice were dosed orally with 0.2 ml 0.25% methyl cellulose solution containing 1% cholesterol and 2 µCi [$^3$H]-cholesterol per mouse. Three hours later, the animals were euthanized, and liver and blood were collected. Cholesterol counts in liver and plasma were determined, and percent inhibition of cholesterol absorption was calculated. Both ezetimibe and 7b inhibited cholesterol absorption by >90% at the lowest dose tested.

Additionally, 7b was tested for inhibition of cholesterol absorption in rats, and its activity was compared to that of ezetimibe-glucuronide. Rats were anesthetized with 100 mg/kg Inactin i.p. The intestine was cannulated by passing an 18G Venocatheter through the fundus of the stomach and approximately 1-2 cm into the duodenum. The cannula was ligated in place at the pyloric valve. Rats were given either 1 ml of rat bile or test compound, 7b or ezetimibe-glucuronide (0.3-30 µg/kg) in 1 ml rat bile. Vehicle or drug remaining in the cannula after delivery was rinsed into the intestine with 1 ml saline. Within 30 minutes of compound or vehicle delivery, 3 ml of a solution containing 1 µCi $^{14}$C— cholesterol in lipid emulsion was delivered to the intestine via the cannula. After 1.5 hours, the rats were euthanized under anesthesia, and blood and liver were collected. Cholesterol counts in liver and plasma were determined, and percent inhibition of cholesterol absorption was calculated. The two test compounds exhibited similar potency for inhibition of cholesterol absorption in this model.

The compounds of structural Formula I of the present invention can be prepared according to the procedures of the following Scheme and Examples, using appropriate materials, and are further exemplified by specific examples which follow. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds.

A variety of chromatographic techniques may be employed in the preparation of the compounds. These techniques include, but are not limited to: High Performance Liquid Chromatography (including normal- reversed- and chiral-phase); Super Critical Fluid Chromatography; preparative Thin Layer Chromatography; flash chromatography with silica gel or reversed-phase silica gel; ion-exchange chromatography; and radial chromatography. All temperatures are degrees Celsius unless otherwise noted.

Some abbreviations used herein include:
Ac Acyl ($CH_3C(O)$—)
Aq. aqueous
Bn benzyl
C. Celsius
calc. Calculated
Celite Celite™ diatomaceous earth
Dess-Martin Periodinane 1,1,1-tris(acetyloxy)-1,1-dihydro-1,2-benzodoxol-3-(1H)-one
DMF N,N-dimethylformamide
equiv. Equivalent(s)
ES-MS Electron Spray Ion-Mass Spectroscopy
EtOAc Ethyl acetate
h Hour(s)
HPLC High performance liquid chromatography
min Minute(s)
m.p. Melting point
MS Mass spectrum
Prep. preparative
r.t. (or rt) Room temperature
sat. saturated
TBS Tert-butyl dimethylsilyl
TFA Trifluoroacetic acid
THF Tetrahydrofuran
Tlc Thin layer chromatography
UDPGA uridine-5'-diphosphoglucuronic acid The general Scheme below illustrates a method for the syntheses of compounds of the present invention of structural formula I-4. All substituents are as defined above in Formula I unless indicated otherwise. In this method, I-1 is treated with a terminal alkyne of type I-2 in the presence of a suitable palladium catalyst such as tetrakistriphenylphosphine palladium(0) or [1,1'-bis(diphenylphosphino)ferrocene]dichloropalladium(II) or the like, and copper(I) iodide. The reaction is usually performed in an inert organic solvent such as DMF, between room temperature and 100° C., for a period of 6-48 h, and the product is an internal alkyne of structural formula I-3. Alkyne I-2 may contain a radioactive atom such as $^{35}S$ to provide the corresponding radiolabeled adduct upon reaction with I-1. Conversion of I-3 to I-4 can be achieved using a variety of hydrolytic methods known to those skilled in the art of organic synthesis. For example, a particularly mild hydrolysis protocol involves the treatment of I-3 with a tertiary amine base such as triethylamine, or diisopropylethylamine or the like, in a mixed solvent system comprising methanol and water. The product of the reaction is a compound of structural formula I-4.

SCHEME

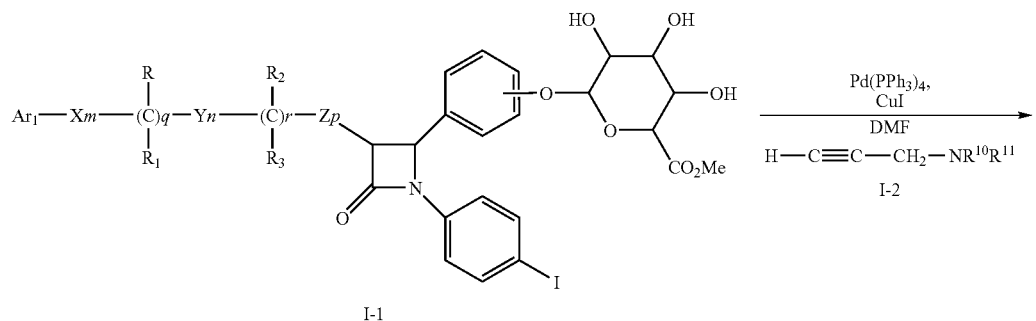

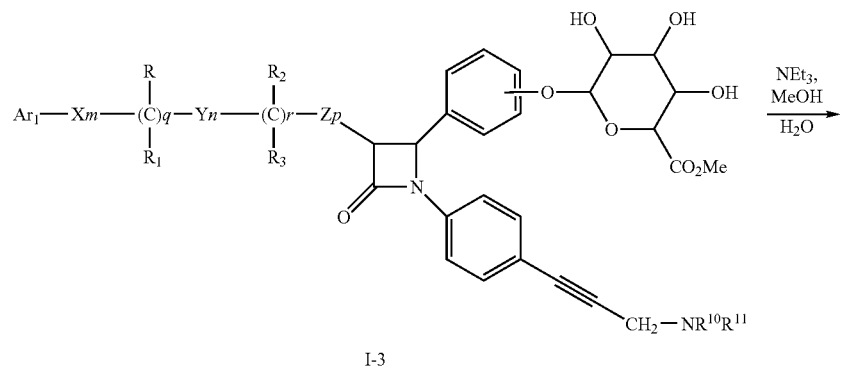

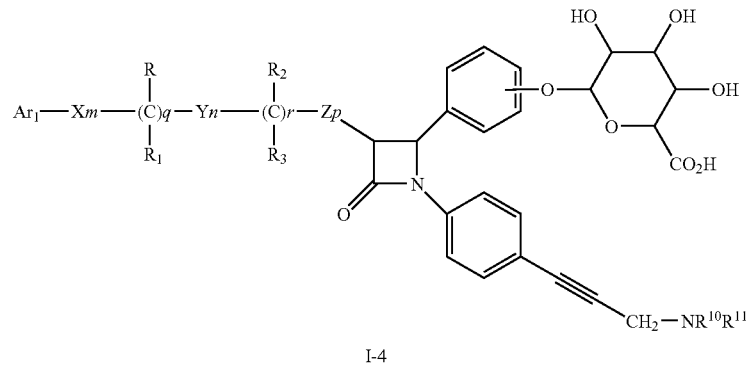

The following examples are provided to illustrate the invention and are not to be construed as limiting the scope of the invention in any matter. The following designations are used in the Examples for certain repetitively used intermediates:

i-1
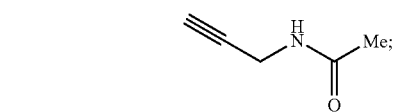

i-2
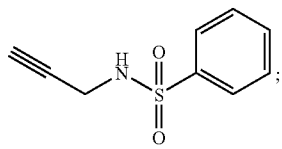

i-3
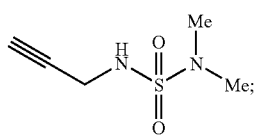

i-4
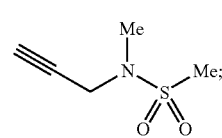

i-5
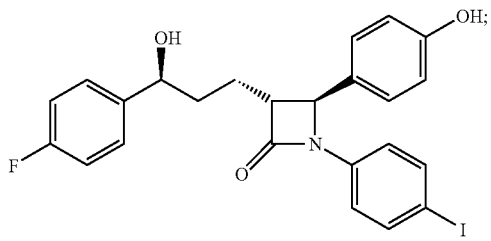

i-6
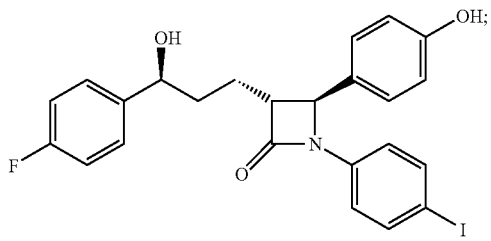

i-7
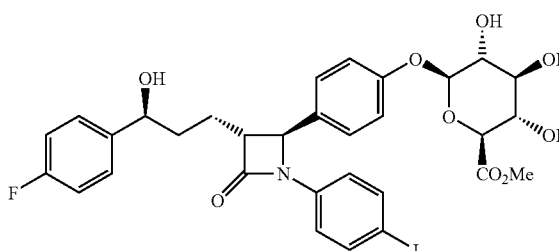

i-8
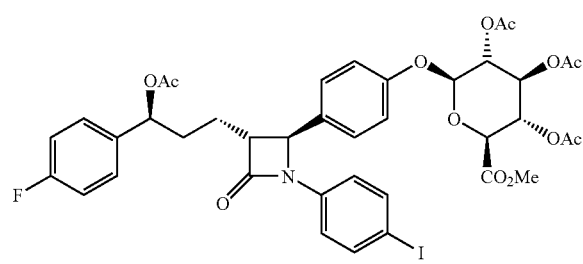

i-9
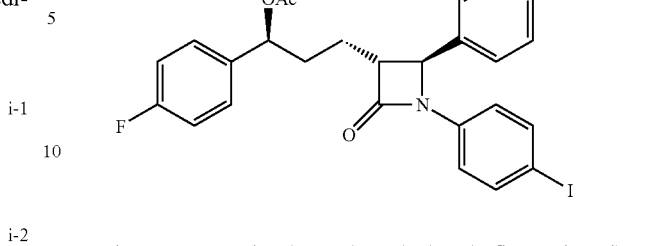

The compounds (3R,4S)-3-[(3S)-3-(4-fluorophenyl)-3-hydroxypropyl]-4-(4-hydroxyphenyl)-1-(4-iodophenyl)azetidin-2-one (i-6) and 4-[(2S,3R)-3-[(3S)-3-(4-fluorophenyl)-3-hydroxypropyl]-1-(4-iodophenyl)-4-oxoazetidin-2-yl] phenyl methyl β-D-glucopyranosiduronate (i-7) were prepared according to Burnett, D. S.; Caplen, M. A.; Domalski, M. S.; Browne, M. E.; Davis, H. R. Jr.; Clader, J. W. Bioorg. Med. Chem. Lett. (2002), 12, 311. Compound i-8 is the hydroxy-protected analog of i-7, where the protecting group is acyl. Similarly, compound i-9 is the hydroxyl-protected analog of i-6 where the protecting group is acyl.

The following definitions are also used in the Examples:

W =
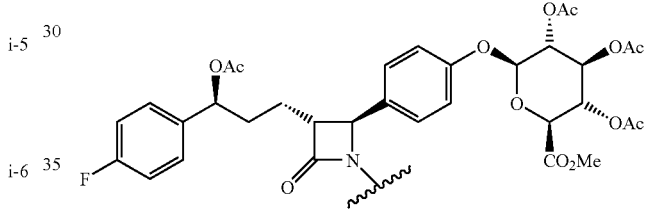

W¹ =
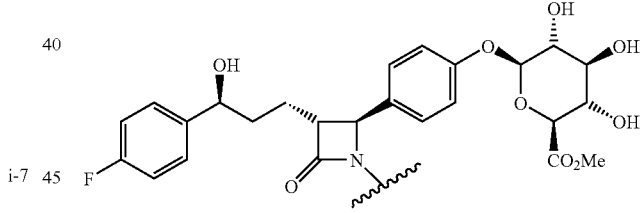

W² =
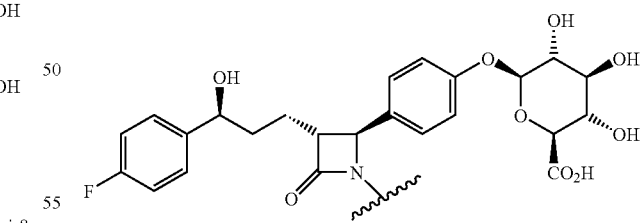

EXAMPLE 1

Preparation of N-prop-2-yn-1-ylacetamide (i-1)

Acetyl chloride (0.52 mL, 7.3 mmol) was added to a stirred solution of propargylamine (0.5 mL, 7.3 mmol) and dimethylaminopyridine (18 mg, 0.14 mmol) in pyridine (2.5 mL) at 0° C., and the resulting mixture was allowed to warm to ambient temperature. After approximately 15 h, the reaction mixture was diluted with ethyl acetate and washed successively with 1N HCl and brine. The organic phase was dried (Na$_2$SO$_4$), filtered and concentrated in vacuo to afford the title compound (i-1), which was used without further purification.

EXAMPLE 2

Preparation of N-prop-2-yn-1-ylbenzenesulfonamide (i-2)

Benzene sulfonyl chloride (1.16 mL, 9.1 mmol) was added to stirred solution of propargylamine (0.62 mL, 9.1 mmol) and dimethylaminopyridine (22 mg, 0.18 mmol) in pyridine (5 mL) at room temperature. The resulting solution was aged at ambient temperature for approximately 15 h. The reaction mixture was diluted with ethyl acetate and washed successively with 1N HCl and brine. The organic phase was dried (Na$_2$SO$_4$), filtered and concentrated in vacuo to furnish the title compound (i-2), which was used without further purification.

EXAMPLE 3

Preparation of N,N-Dimethyl-N'-prop-2-yn-1-ylurea (i-3)

Dimethyl carbamylchloride (0.84 mL, 9.1 mmol) was added to a stirred solution of propargylamine (0.62 mL, 9.1 mmol) and dimethylaminopyridine (22 mg, 0.18 mmol) in pyridine (5 mL) at room temperature. The resulting suspension was stirred at ambient temperature for approximately 15 h. The reaction mixture was diluted with ethyl acetate and washed successively with 1N HCl and brine. The organic phase was dried (Na$_2$SO$_4$), filtered and concentrated in vacuo to afford the title compound (i-3), which was used without further purification.

EXAMPLE 4

Preparation of N-Methyl-N-prop-2-yn-1-ylmethanesulfonamide (i-4)

Methansulfonylchloride (1.12 mL, 14.5 mmol) was added to a stirred solution of N-methylpropargylamine (1.22 mL, 14.5 mmol) and dimethylaminopyridine (35 mg, 0.30 mmol) in pyridine (10 mL) at room temperature. After aging for approximately 15 h, the reaction mixture was poured into ethyl acetate and washed successively with 1N HCl and brine. The organic phase was dried (Na$_2$SO$_4$), filtered and concentrated in vacuo, to afford the title compound (i-4), which was used without further purification.

EXAMPLE 5

Preparation of N-prop-2-yn-1-ylmethanesulfonamide (i-5)

Methansulfonylchloride (1.40 mL, 18.1 mmol) was added dropwise to a stirred solution of propargylamine (1.00 g, 18.1 mmol) and dimethylaminopyridine (44.0 mg, 0.36 mmol) in pyridine (10 mL) at 0° C. After aging for approximately 15 h, the reaction mixture was poured into 1N HCl and extracted twice with ethyl acetate. The combined organic extracts were washed with saturated aqueous sodium bicarbonate, brine, dried (MgSO$_4$), filtered and concentrated in vacuo, to afford the title compound i-5. Crude i-5 crystallized on standing and was used without further purification.

EXAMPLE 6

Preparation of N-(3-{4-[(2S,3R)-3-[(3S)-3-(4-fluorophenyl)-3-hydroxypropyl]-2-(4-hydroxyphenyl)-4-oxoazetidin-1-yl]phenyl}prop-2-yn-1-yl)methanesulfonamide (Compound 6a)

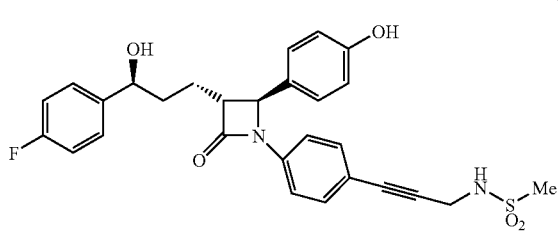

6a

Triethylamine (7 equivalents) is added to a solution of (3R,4S)-3-[(3S)-3-(4-fluorophenyl)-3-hydroxypropyl]-4-(4-hydroxyphenyl)-1-(4-iodophenyl)azetidin-2-one (i-6) (1.00 equivalent), N-prop-2-yn-1-ylmethanesulfonamide (i-5) (1.50 equivalents), tetrakistriphenylphosphine palladium(0) (0.15 equivalents) and copper(I) iodide (0.30 equivalents) in DMF (0.1 M concentration with respect to final product) under a nitrogen atmosphere and the resulting solution aged at room temperature. After completion of reaction, the volatiles are evaporated in vacuo and the crude residue can be purified by flash chromatography on silica gel to afford the title compound.

Alternate preparation of 6a:

Step A: Preparation of (1S)-3-[(2S,3R)-2-(4-{[tert-butyl(dimethyl)silyl]oxy}phenyl)-1-(4-iodophenyl)-4-oxoazetidin-3-yl]-1-(4-fluorophenyl)propyl acetate

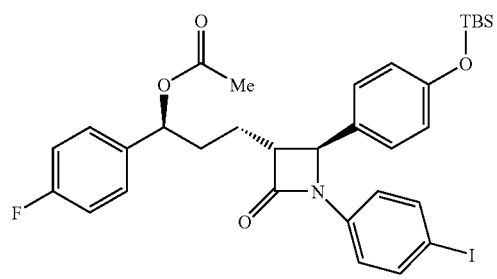

To a solution of 0.5 g. (0.894 mmol, 1 equiv.) (3R,4S)-3-[(3S)-3-(4-fluorophenyl)-3-hydroxypropyl]-4-(4-hydroxyphenyl)-1-(4-iodophenyl)azetidin-2-one (i-6) in 5 mL anhydrous methylene chloride under inert atmosphere at 0° C. was added 0.36 mL (1.564 mmol, 1.75 equiv.) tert-butyldimethylsilyl trifluoromethanesulfonate, 0.175 mL (0.894 mmol, 1 equiv.) N-tert-butyldimethylsilylimidazole and 0.311 mL (2.234 mmol, 2.5 equivalents) triethylamine. The resulting reaction mixture was stirred at 0° C. for 15 minutes then quenched by the addition of 5 mL of sat. aq. solution of sodium carbonate. The resulting mixture was transferred to a separatory funnel, extracted with methylene chloride (3×5 mL). The combined organic extracts were dried over anhydrous Na$_2$SO$_4$ filtered and the solvent removed under vacuum. The residue was purified by prep. Tlc eluting with EtOAc/hexanes (2/1) to afford the title compound. m/z (ES) 696.0 (M+Na$^+$), 614.0 (M–OAc$^+$).

Step B: Preparation of (1S)-3-[(2S,3R)-2-(4-{[tert-butyl(dimethyl)silyl]oxy}phenyl)-1-(4-{3-[(methylsulfonyl)amino]prop-1-yn-1-yl}phenyl)-4-oxoazetidin-3-yl]-1-(4-fluorophenyl)propyl acetate

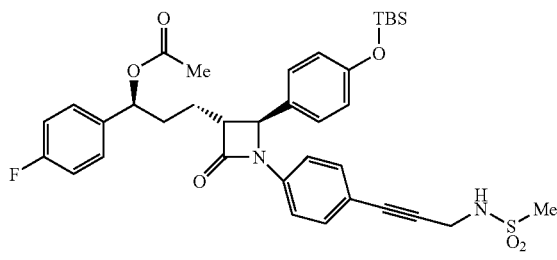

A solution of 0.5 g (0.742 mmol, 1 equiv) (1S)-3-[(2S,3R)-2-(4-{[tert-butyl(dimethyl)silyl]oxy}phenyl)-1-(4-iodophenyl)-4-oxoazetidin-3-yl]-1-(4-fluorophenyl)propyl acetate (intermediate of step A), 0.198 g (1.48 mmol, 2 equiv.) N-prop-2-yn-1-ylmethanesulfonamide (i-5), 0.086 g (0.074 mmol, 0.1 equiv.) tetrakistriphenylphosphine palladium(0) and 7 mg (0.04 mmol, 0.05 equiv) copper(I) iodide in 8 mL methylene chloride was deoxygenated by a slow stream of anhydrous nitrogen delivered by a needle through a rubber septum. To the resulting solution was added by syringe 1 mL (7.42 mmol, 10 equiv.) triethylamine. The resulting solution was stirred at room temperature for 4.5 hr at which time the mixture was partitioned 5 mL of a 5% aq. solution of citric acid. The mixture was transferred to a spearatory funnel and extracted with EtOAc (3×5 mL) and methylene chloride (2×5 mL) The combined organic extracts were dried over anhydrous Na$_2$SO$_4$ filtered and the solvent removed under vacuum. The residue was purified by prep. Tlc eluting with EtOAc/hexanes (4/1) followed by further purification by prep. Tlc eluting with EtOAc/hexanes (1/1) to afford the title compound. m/z (ES) 619.0 (M–HOAc$^+$).

Step C: Preparation of N-[3-(4-{(2S,3R)-2-(4-{[tert-butyl(dimethyl)silyl]oxy}phenyl)-3-[(3S)-3-(4-fluorophenyl)-3-hydroxypropyl]-4-oxoazetidin-1-yl}phenyl)prop-2-yn-1-yl]methanesulfonamide

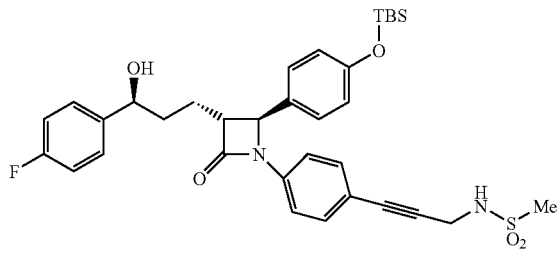

To a solution of 40 mg (0.059 mmol) (1S)-3-[(2S,3R)-2-(4-{[tert-butyl(dimethyl)silyl]oxy}phenyl)-1-(4-{3-[(methylsulfonyl)amino]prop-1-yn-1-yl}phenyl)-4-oxoazetidin-3-yl]-1-(4-fluorophenyl)propyl acetate (intermediate of step B) in 1 mL anhydrous methanol under nitrogen atmosphere was added 1 mg of sodium cyanide. The reaction mixture was heated at 50° C. for 4 hrs at which time the volatiles were removed by a nitrogen stream. The residue was purified by prep. Tlc eluting with EtOAc/hexanes (3/1) to afford the title compound. m/z (ES) 637.2 (MH$^+$), 619.1 M–H$_2$O$^+$).

Step D: Preparation of Compound 6a

To a solution of 10 mg of N-[3-(4-{(2S,3R)-2-(4-{[tert-butyl(dimethyl)silyl]oxy}phenyl)-3-[(3S)-3-(4-fluorophenyl)-3-hydroxypropyl]-4-oxoazetidin-1-yl}phenyl)prop-2-yn-1-yl]methanesulfonamide in 0.5 mL THF was added 0.5 mL of 2N aq. HCl. The resulting mixture was stirred at room temperature for 1 hr at which time the volatiles were removed under vacuum. The residue was purified by prep. Tlc eluting with CH$_2$Cl$_2$/MeOH (9/1) followed by further purification by prep. Tlc eluting with CH$_2$Cl$_2$/MeOH (95/5) afforded the title compound. m/z (ES) 544.9 (M+Na$^+$), 523 (MH$^+$), 505 (M–H$_2$O$^+$).

EXAMPLE 7

Step A: Preparation of 4-[(2S,3R)-3-[(3S)-3-(4-fluorophenyl)-3-hydroxypropyl]-1-(4-{3-[(methylsulfonyl)amino]prop-1-yn-1-yl}phenyl)-4-oxoazetidin-2-yl]phenyl methyl β-D-glucopyranosiduronate (Compound 7a)

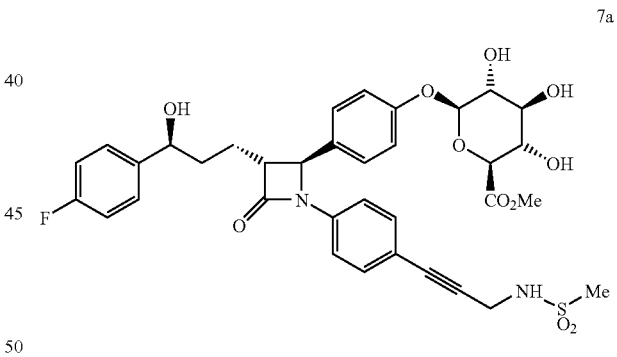

Triethylamine (0.07 mL, 0.502 mmol) was added to a stirred solution of 4-[(2S,3R)-3-[(3S)-3-(4-fluorophenyl)-3-hydroxypropyl]-1-(4-iodophenyl)-4-oxoazetidin-2-yl]phenyl methyl β-D-glucopyranosiduronate (i-7) (0.050 g, 0.071 mmol), N-prop-2-yn-1-ylmethanesulfonamide (i-5) (0.014 g, 0.105 mmol), tetrakistriphenylphosphine palladium(0) (0.012 g, 0.010 mmol) and copper iodide (0.005 g, 0.026 mmol) in DMF (0.5 mL) under a nitrogen atmosphere and the resulting solution aged at room temperature for 18 h. The volatiles were evaporated in vacuo and the crude residue purified by flash chromatography on silica gel (gradient elution; 0-25% methanol/methylene chloride as eluent) to afford the title compound; m/z (ES) 713 (MH$^+$), 505.

Step B: Preparation of 4-[(2S,3R)-3-[(3S)-3-(4-fluorophenyl)-3-hydroxypropyl]-1-(4-{3-[(methylsulfonyl)amino]prop-1-yn-1-yl}phenyl)-4-oxoazetidin-2-yl]phenyl β-D-glucopyranosiduronic acid (Compound 7b)

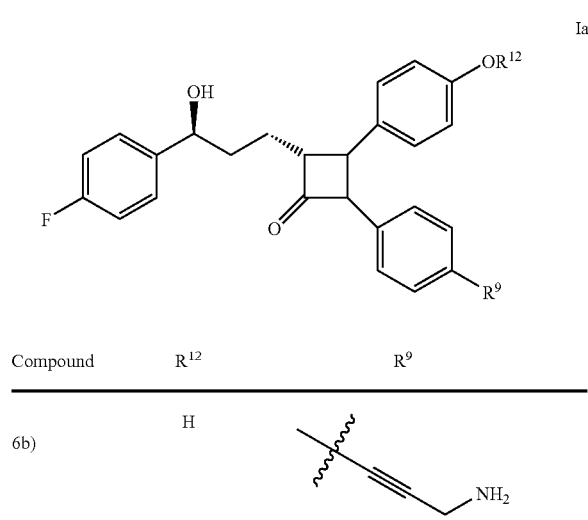

A solution of compound 7a in methanol/water/triethylamine (1:7:2; 1 mL) was stirred at room temperature for approximately 1.5 h. The volatiles were evaporated in vacuo and the crude residue purified by preparative reversed phase high performance liquid chromatography on YMC Pack Pro C18 phase (gradient elution; 10-65% acetonitrile/water as eluent, 0.1% TFA modifier) to give the title compound (7b); m/z (ES) 699 (MH$^+$), 505; KRMS (ES) m/z calcd for $C_{34}H_{36}FN_2O_{11}S$ (MH$^+$) 699.2024, found 699.2016.

EXAMPLES 6b TO 6g AND 7c TO 7n

The following compounds of Formula Ia have been prepared (as indicated by MS data provided) or can be prepared using the general synthetic procedures described in Example 6 (shown in Table 1) or Example 7 (shown in Table 2).

TABLE 1

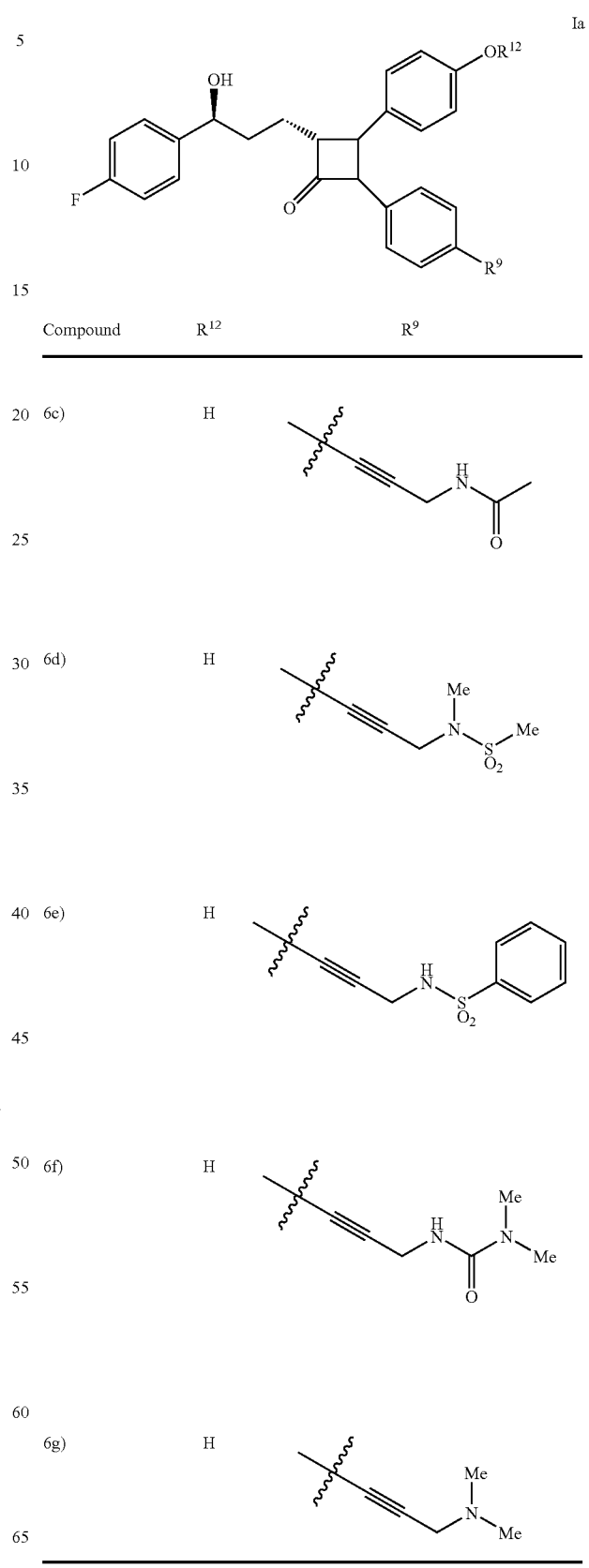

TABLE 2

| Compound | R¹² | R⁹ | m/z (ES) | HRMS m/z (ES) |
|---|---|---|---|---|
| 7c) | methyl ester glucuronide | alkyne-CH₂-NH₂ | 658 (MNa⁺) | |
| 7d) | glucuronide | alkyne-CH₂-NH₂ | 621 (MH⁺) | (MH⁺) Calcd 621.2249 Found 621.2223 |
| 7e) | methyl ester glucuronide | alkyne-CH₂-NHC(O)Me | 677 (MH⁺) | |
| 7f) | glucuronide | alkyne-CH₂-NHC(O)Me | 663 (MH⁺) | (MH⁺) Calcd 663.2354 Found 663.2331 |
| 7g) | methyl ester glucuronide | alkyne-CH₂-N(Me)SO₂Me | 749 (MNa⁺) | |
| 7h) | glucuronide | alkyne-CH₂-N(Me)SO₂Me | 735 (MNa⁺) | (MH⁺) Calcd 713.2180 Found 713.2170 |
| 7i) | methyl ester glucuronide | alkyne-CH₂-NHSO₂Ph | 797 (MNa⁺) | |
| 7j) | glucuronide | alkyne-CH₂-NHSO₂Ph | 783 (MNa⁺) | (MH⁺) Calcd 761.2180 Found 761.2193 |
| 7k) | methyl ester glucuronide | alkyne-CH₂-NHC(O)NMe₂ | 706 (MH⁺) | |
| 7l) | glucuronide | alkyne-CH₂-NHC(O)NMe₂ | 692 (MH⁺) | (MH⁺) Calcd 692.2620 Found 692.2618 |

TABLE 2-continued

| Compound | $R^{12}$ | $R^9$ | m/z (ES) | HRMS m/z (ES) |
|---|---|---|---|---|
| 7m) | methyl ester glucuronide | ![structure with alkyne-CH2-N(Me)2] | 663 (MH+) | |
| 7n) | glucuronide | ![structure with alkyne-CH2-N(Me)2] | 649 (MH+) | (MH+) Calcd 649.2562 Found 649.2532 |

EXAMPLE 8

Step A: Preparation of 4-((2S,3R)-3-[(3S)-3-(4-fluorophenyl)-3-hydroxypropyl]-4-oxo-1-{4-[(trimethylsilyl)ethynyl]phenyl}azetidin-2-yl)phenyl methyl β-D-glucopyranosiduronate (8a)

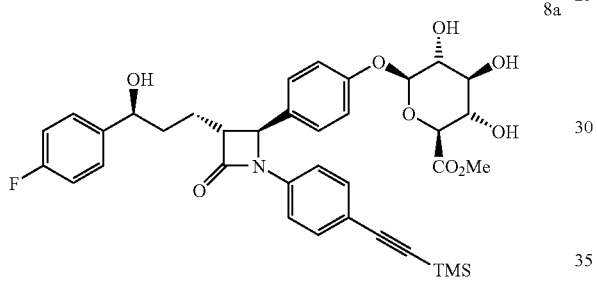

8a

Triethylamine (69.0 μL, 0.495 mmol) was added to a stirred solution of i-7 (50.0 mg, 0.071 mmol), trimethylsilyacetylene (12.0 μL, 0.085 mmol), tetrakistriphenylphosphine palladium(0) (13.0 mg, 0.011 mmol) and copper iodide (5.10 mg, 0.028 mmol) in DMF (0.5 mL) under a nitrogen atmosphere and the resulting solution aged at room temperature for 18 h. The volatiles were evaporated in vacuo and the crude residue purified by flash chromatography on silica gel (gradient elution; 0-25% methanol/methylene chloride as eluent) to afford the title compound (8a); m/z (ES) 660 (M–OH)+, 470.

Step B: Preparation of 4-{(2S,3R)-1-(4-ethynylphenyl)-3-[(3S)-3-(4-fluorophenyl)-3-hydroxypropyl]-4-oxoazetidin-2-yl}phenyl β-D-glucopyranosiduronic acid (8b)

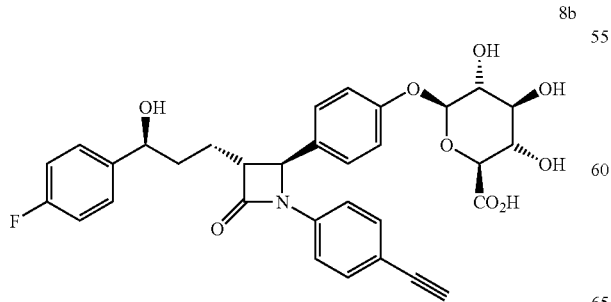

8b

A solution of 8a in methanol/water/triethylamine (0.25 mL:1.10 mL:0.40 mL) was stirred at room temperature for approximately 6 h. The volatiles were evaporated in vacuo and the crude residue purified by preparative reversed phase high performance liquid chromatography on YMC Pack Pro C18 phase (gradient elution; 10-65% acetonitrile/water as eluent, 0.1% TFA modifier) to give the title compound (fb); m/z (ES) 574 (M–OH)+, 398; HRMS (ES) m/z calc'd for $C_{32}H_{31}FNO_9$ (MH+) 592.1983, found 592.1985.

EXAMPLE 9

Step A: Preparation of 4-[(2S,3R)-3-[(3S)-3-(4-fluorophenyl)-3-hydroxypropyl]-1-(4-{3-[(methylsulfonyl)amino]propyl}phenyl)-4-oxoazetidin-2-yl]phenyl methyl β-D-glucopyranosiduronate (9a)

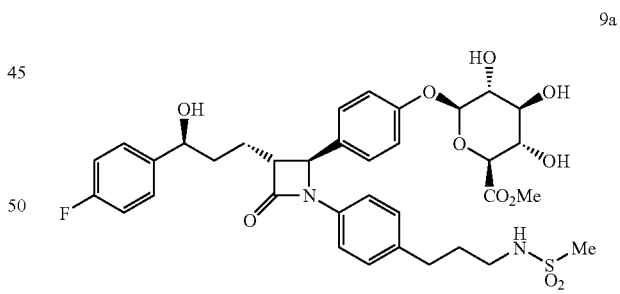

9a

A mixture of 7a (40.0 mg, 0.056 mmol) and palladium (~8 mg of 10 wt. % (dry basis) on activated carbon) in methanol (2 mL) was hydrogenated at atmospheric pressure for approximately 1 h. The reaction mixture was filtered through a short plug of celite, eluting copiously with methanol, and the filtrate evaporated in vacuo to afford the title compound (9a); m/z (ES) 509 (M-sugar-OH)+. HRMS (ES) m/z calcd. for $C_{34}H_{39}FN_2O_{11}S$(MH+) 703.2337, found 703.2337.

Step B: Preparation of 4-[(2S,3R)-3-[(3S)-3-(4-fluorophenyl)-3-hydroxypropyl]-1-(4-{3-[(methylsulfonyl)amino]propyl}phenyl)-4-oxoazetidin-2-yl]phenyl β-D-glucopyranosiduronic acid (9b)

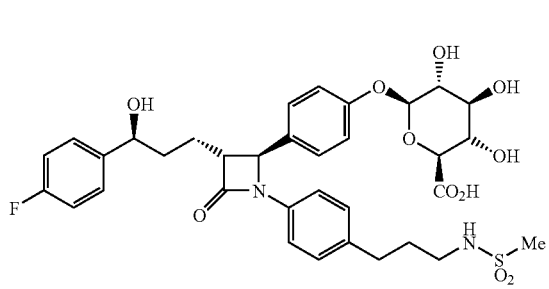

9b

A solution of 9a in methanol/water/triethylamine (1:7:2, 1 mL) was stirred at room temperature for approximately 1 h. The volatiles were evaporated in vacuo and the crude residue purified by preparative reversed phase high performance liquid chromatography on YMC Pack Pro C18 phase (gradient elution; 10-65% acetonitrile/water as eluent, 0.1% TFA modifier) to give the title compound (2b; m/z (ES) 735 (M+Na)$^+$, 685 (M−OH)$^+$, 509 (M-sugar-OH)$^+$; HRMS (ES) m/z calc'd for $C_{34}H_{39}FN_2O_{11}S$ (MH$^+$) 703.2337, found 703.2337.

EXAMPLE 10

Step A: Preparation of 4-{(2S,3R)-3-[(3S)-3-acetoxy)-3-(4-fluorophenyl)propyl]-1-[4-(3-{[tert-butyl(dimethylsilyl]oxy}prop-1-yn-1-yl)phenyl]-4-oxoazetidin-2-yl}phenyl methyl 2,3,4-tri-O-acetyl-β-D-glucopyranosiduronate (10a)

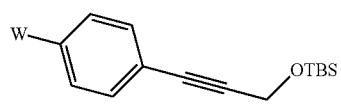

10a

Triethylamine (170 μL, 1.25 mmol) was added to a solution of i-8 (156 mg, 0.178 mmol), tert-butyldimethyl(2-propynyloxy)silane (43.0 μL, 0.214 mmol), dichlorobistriphenylphosphine palladium(II) (12.0 mg, 0.018 mmol) and copper iodide (7.00 mg, 0.036 mmol) in DMF (1.3 mL) under a nitrogen atmosphere and the resulting solution aged at room temperature for approximately 20 h. The reaction mixture was poured into saturated aqueous sodium bicarbonate and extracted twice with diethyl ether. The combined organic extracts were washed with water, brine, dried (MgSO$_4$), filtered and the filtrate concentrated in vacuo. Purification of the crude residue by flash chromatography on silica gel (gradient elution; 15-40% ethyl acetate/hexanes as eluent) afforded the title compound 10a.

Step B: Preparation of 4-{(2S,3R)-3-[(3S)-3-(acetyloxy)-3-(4-fluorophenyl)propyl]-1-[4-(3-hydroxyprop-1-yn-1-yl)phenyl]-4-oxoazetidin-2-yl}phenyl methyl 2,3,4-tri-O-acetyl-β-D-glucopyranosiduronate (10b)

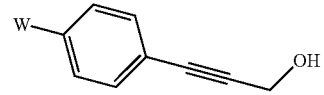

10b

Tetrabutylammonium fluoride hydrate (39.0 mg, 0.148 mmol) was added to 10a (136 mg, 0.148 mmol) in tetrahydrofuran (1.5 mL), and the resulting solution aged at room temperature for 1 h. The reaction mixture was poured into saturated aqueous ammonium chloride and extracted twice with ether. The combined organic extracts were washed with saturated sodium bicarbonate, brine, dried (MgSO$_4$), filtered and concentrated in vacuo. Purification of the crude residue by flash chromatography on silica gel (50% ethyl acetatel-hexanes) afforded the title compound 10b.

Step C: Preparation of 4-{(2S,3R)-3-[(3S)-3-(acetyloxy)-3-(4-fluorophenyl)propyl]-4-oxo-1-[4-(3-oxoprop-1-yn-1-yl)phenyl]azetidin-2-yl}phenyl methyl 2,3,4-tri-O-acetyl-β-D-glucopyranosiduronate (10c)

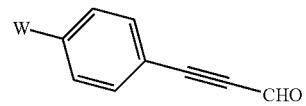

10c

Dess-Martin periodinane (33.0 mg, 0.077 mmol) was added to a solution of 10b (62.0 mg, 0.077 mmol) and pyridine (31.0 μL, 0.386 mmol) in dichloromethane (1 mL) at room temperature. After 30 min, the reaction mixture was poured into saturated aqueous sodium bicarbonate, and extracted twice with ethyl acetate. The combined organic extracts were washed with water, brine, dried (MgSO$_4$), filtered and concentrated in vacuo. Purification of the crude residue by flash chromatography on silica gel (gradient elution; 20-40% ethyl acetate/hexanes) afforded the title compound 10c.

Step D: Preparation of 4-{(2S,3R)-3-[(3S)-3-(acetyloxy)-3-(4-fluorophenyl)propyl]-1-[4-(carboxyethynyl)phenyl]-4-oxoazetidin-2-yl}phenyl methyl 2,3,4-tri-O-acetyl-β-D-glucopyranosiduronate (10d)

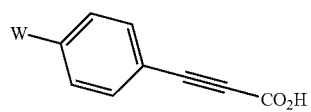

10d

An aqueous solution (0.1 mL) of sodium dihydrogenphosphate (9.00 mg, 0.065 mmol) and sodium chlorite (5.00 mg, 0.055 mmol) was added to a solution of 10c (37.0 mg, 0.046 mmol) in tert-butyl alchohol (0.4 mL), dioxane (0.2 mL) and isobutylene (~0.1 mL) at room temperature. After 1.5 h, the reaction mixture was concentrated in vacuo and the crude residue triturated repeatedly with ethyl acetate. The organic washings were dried (Na$_2$SO$_4$), filtered and concentrated in vacuo to afford the title compound 10d.

Step E: Preparation of 4-{(2S,3R)-1-[4-(carboxyethynyl)phenyl]-3-[(3S)-3-(4-fluorophenyl)-3-hydroxypropyl]-4-oxoazetidin-2-yl}phenyl β-D-glucopyranosiduronic acid (10e)

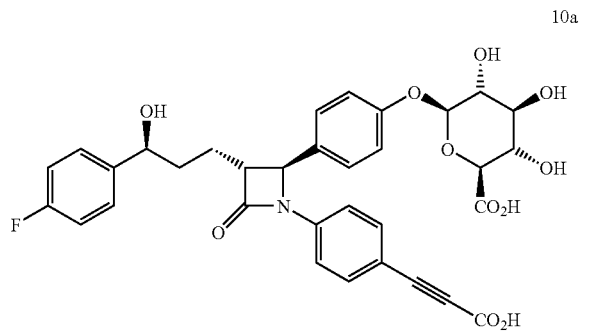

10a

A solution of 4-{(2S,3R)-3-[(3S)-3-(acetyloxy)-3-(4-fluorophenyl)propyl]-1-[4-(carboxyethynyl)phenyl]-4-oxoazetidin-2-yl}phenyl methyl 2,3,4-tri-O-acetyl-β-D-glucopyranosiduronate (10d) and sodium cyanide (~1 mg, 0.020 mmol) in methanol (3 mL) was heated to 45° C. After 22 h, the reaction mixture was concentrated under reduced pressure and dissolved in methanol/water/triethylamine (1:7:2, 1 mL). After stirring at room temperature for approximately 1 h, the volatiles were evaporated in vacuo and the crude residue purified by preparative reversed phase high performance liquid chromatography on YMC Pack Pro C18 phase (gradient elution; 10-60% acetonitrile/water as eluent, 0.1% TFA modifier) to give the title compound (10e), m/z (ES) 442.0 (M-sugar-OH)$^+$, 618.0 (M−OH)$^+$; HRMS (ES) m/z calcd. for C$_{33}$H$_{31}$FNO$_{11}$ (MH$^+$) 636.1881, found 636.1889

EXAMPLE 11

Step A: Preparation of 4-((2S,3R)-3-[(3S)-3-(acetyloxy)-3-(4-fluorophenyl)propyl]-1-{4-(3-(ethylamino)-3-oxoprop-1-yn-1-yl]phenyl}-4-oxoazetidin-2-yl)phenyl methyl 2,3,4-tri-O-acetyl-β-D-glucopyranosiduronate (11a)

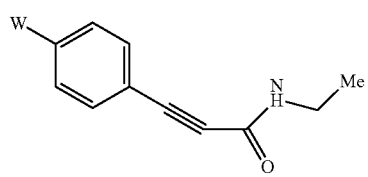

11a

A 1M solution of ethylamine hydrochloride and diisopropylethylamine in DMF (40.0 µL, 0.40 mmol) was added to 4-{(2S,3R)-3-[(3S)-3-(acetyloxy)-3-(4-fluorophenyl)propyl]-1-[4-(carboxyethynyl)phenyl]-4-oxoazetidin-2-yl}phenyl methyl 2,3,4-tri-O-acetyl-β-D-glucopyranosiduronate (10d) (27.0 mg, 0.033 mmol), 1-[3-(dimethylamino)propyl]-3-ethylcarbodiimide hydrochloride (19.0 mg, 0.099 mmol) and 1-hydroxybenzotriazole (8.00 mg, 0.059 mmol) in DMF (0.25 mL). After 4.5 h, the reaction mixture was poured into ethyl acetate and washed successively with water and brine. The organic layer was dried, filtered and concentrated under reduced pressure. Purification of the crude residue by flash chromatography on silica gel (gradient elution; 50-60% ethyl acetate/hexanes) afforded the title compound 11a.

Step B: Preparation of 4-{(2S,3R)-1-{4-[3-(ethylamino)-3-oxoprop-1-yn-1-yl]phenyl}-3-[(3S)-3-(4-fluorophenyl)-3-hydroxypropyl]-4-oxoazetidin-2-yl}phenyl β-D-glucopyranosiduronic acid (11b)

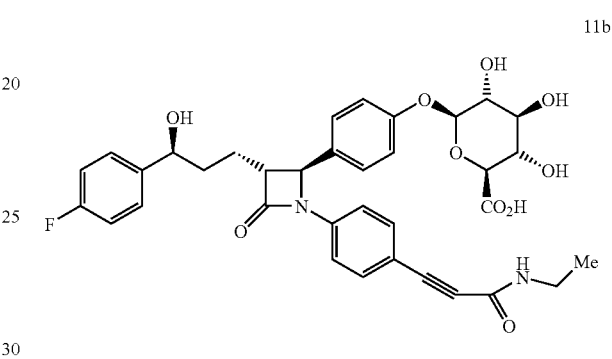

11b

A solution of 4-((2S,3R)-3-[(3S)-3-(acetyloxy)-3-(4-fluorophenyl)propyl]-1-{4-(3-(ethylamino)-3-oxoprop-1-yn-1-yl]phenyl}-4-oxoazetidin-2-yl)phenyl methyl 2,3,4-tri-O-acetyl-β-D-glucopyranosiduronate (11a) (22.0 mg, 0.026 mmol) and sodium cyanide (~1 mg, 0.020 mmol) in methanol (3 mL) was heated to 45° C. After 18 h, the reaction mixture was concentrated under reduced pressure and dissolved in methanol/water/triethylamine (1:3:1, 2.5 mL). After stirring at room temperature for approximately 1 h, the volatiles were evaporated in vacuo, and the crude residue purified by preparative reversed phase high performance liquid chromatography on YMC Pack Pro C18 phase (gradient elution; 10-60% acetonitrile/water as eluent, 0.1% TFA modifier) to give the title compound (11b) m/z (ES) 663.0 (M+H)$^+$; HRMS (ES) m/z calcd. for C$_{35}$H$_{36}$FN$_2$O$_{10}$ (MH$^+$) 663.2354, found 663.2341.

EXAMPLE 12

Step A: Preparation of [$^{35}$S]N-prop-2-yn-1-yl-methanesulfonamide

The appropriate volume of [$^{35}$S]methane sulfonyl chloride (see Dean, D. C.; et al., J. Med. Chem. 1996, 39, 1767) totaling 3.5 mCi was removed from a stock solution in methylene chloride and placed in a 5 mL conical flask. It was then distilled at atmospheric pressure until the volume was approximately 50 µL. To this solution was immediately added 50 µL of propargylamine. After 15 min, the reaction mixture was diluted with 10 mL of ethyl acetate, washed with saturated sodium bicarbonate solution (3×2 mL), and dried over sodium sulfate. After filtration the resulting solution had a count of 3.3 mCi and a radiochemical purity of 99.9% by HPLC (Zorbax XDB C8 column, 4.6×150 mm, 5% acetonitrile:H$_2$O (0.1% TFA) to 100% acetonitrile, 15 min linear gradient, 1 mL/min, t$_R$=4.4 min).

Step B: Preparation of [$^{35}$S] 4-[(2S,3R)-3-[(3S)-3-(4-fluorophenyl)-3-hydroxypropyl]-1-(4-{3-[(methylsulfonyl)amino]prop-1-yn-1-yl}phenyl)-4-oxoazetidin-2-yl]phenyl methyl β-D-glucopyranosiduronate ([$^{35}$S] 7a) {*denotes $^{35}$S}

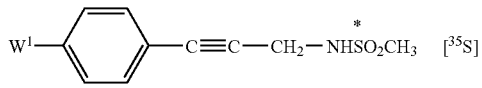

7a

Dissolved 3.0 mCi of [$^{35}$S]N-prop-2-yn-1-ylmethanesulfonamide, 1 mg of compound i-7, and 1 µL of triethylamine in 100 µL of dimethylformamide inside a plastic microcentrifuge tube. To this solution was added 10 µL of a stock solution containing 8.1 mg of tetrakis(triphenylphosphine)palladium(0) and 1.4 mg of copper iodide in 1 mL of dimethylformamide. Stirred at room temperature for sixty hours at which time HPLC indicated 55% conversion. This reaction mixture, which had a radiochemical purity of 44.4% by HPLC (Zorbax XDB C8 column, 4.6×150 mm, 5% acetonitrile:H$_2$O (0.1% TFA) to 100% acetonitrile, 15 min linear gradient, 1 mL/min, t$_R$=9.3 min) was taken on directly to the next step.

Step C: Preparation of [$^{35}$S] 4-[(2S,3R)-3-[(3S)-3-(4-fluorophenyl)-3-hydroxypropyl]-1-(4-{3-[(methylsulfonyl)amino]prop-1-yn-1-yl}phenyl)-4-oxoazetidin-2-yl]phenyl β-D-glucopyranosiduronic acid ([$^{35}$S] 7b)

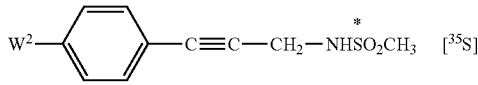

7b

The crude reaction mixture containing compound [$^{35}$S] 7b was treated with 25 µL of methanol, 90 µL of water, and 30 µL of triethylamine and stirred at room temperature for one hour at which time it was concentrated to near dryness under a slow stream of nitrogen. The residue was dissolved in 1:1 acetonitrile:H$_2$O and subjected to semi-preparative chromatography (Zorbax XDB C8 250×9.4 mm column, 70:30 acetonitrile:H$_2$O (0.1% TFA) 4 mL/min, 1×0.2 mL injections). 540 µCi of product was obtained which had a radiochemical purity of 99.9% by HPLC (Zorbax XDB C8 column, 4.6×150 mm, 70:30 acetonitrile:H$_2$O (0.1% TFA), 1 mL/min, t$_R$=10.4 min) and coeluted with an authentic sample of compound 7b. LC/MS m/z=508 (product—glucuronide—H$_2$O), SA=769 Ci/mmol.

Alternate Preparation of [$^{35}$S] 7b:

Step A: Preparation of [$^{35}$S] 7a

The appropriate volume of [$^{35}$S]methane sulfonyl chloride (see Dean, D. C.; et al., J. Med. Chem. 1996, 39, 1767) totaling 1.3 mCi was removed from a stock solution in methylene chloride and placed in a 5 mL conical flask. It was then distilled at atmospheric pressure until the volume was approximately 50 µL. To this solution was immediately added a solution of 1 mg of 13a in 5 µL of pyridine (freshly distilled over calcium hydride).

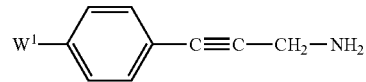

13a

The solution was stirred at room temperature for five minutes at which time it was concentrated to near dryness under a slow stream of nitrogen. This reaction mixture, which had a radiochemical purity of 80.1% by HPLC (Zorbax XDB C8 column, 4.6×150 mm, 5% acetonitrile:H$_2$O (0.1% TFA) to 100% acetonitrile, 15 min linear gradient, 1 mL/min, t$_R$=9.3 min) was taken on directly to the next step.

Step B: Preparation [$^{35}$S] 7b

The crude reaction mixture containing [$^{35}$S] 7a was treated with 25 µL of methanol, 90 µL of water, and 30 µL of triethylamine and stirred at room temperature for one hour at which time it was concentrated to near dryness under a slow stream of nitrogen. The residue was dissolved in 1:1 acetonitrile:H$_2$O and subjected to semi-preparative chromatography (Zorbax XDB C8 250×9.4 mm column, 70:30 acetonitrile:H$_2$O (0.1% TFA) 4 mL/min, 1×0.2 mL injections). 350 µCi of product was obtained which had a radiochemical purity of 98.4% by HPLC (Zorbax XDB C8 column, 4.6×150 mm, 70:30 acetonitrile:H$_2$O (0.1% TFA), 1 mL/min, t$_R$=10.4 min) and coeluted with an authentic sample of 7b. LC/MS m/z=508 (product—glucuronide—H$_2$O), SA=911 Ci/mmol.

Alternate Preparation of [$^{35}$S] 7b:

Step A: Preparation of (3R,4S)-4-(4-{[tert-butyl(dimethyl)silyl]oxy}phenyl)-3-[(3S)-3-(4-fluorophenyl)-3-hydroxypropyl]-1-(4-iodophenyl)azetidin-2-one

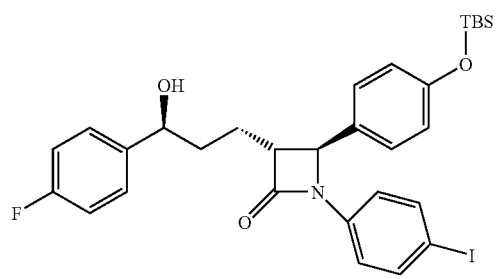

To a solution of 15 mg (0.022 mmol) (1S)-3-[(2S,3R)-2-(4-{[tert-butyl(dimethyl)silyl]oxy}phenyl)-1-(4-iodophenyl)-4-oxoazetidin-3-yl]-1-(4-fluorophenyl)propyl acetate (Alternate Example 6, step A) in 1 mL anhydrous methanol under nitrogen atmosphere was added 2 mg of sodium cyanide. The reaction mixture was heated at 50° C. for 1.25 hr at which time the volatiles were removed by a nitrogen stream. The residue was purified by prep. Tlc eluting with EtOAc/hexanes (1/3) to afford the title compound. m/z (ES) 632.3 (MH$^+$), 614.3 (MH−H$_2$O$^+$).

Step B: Preparation of (3R,4S)-1-[4-(3-aminoprop-1-yn-1-yl)phenyl]-4-(4-{[tert-butyl(dimethyl)silyl]oxy}phenyl)-3-[(3S)-3-(4-fluorophenyl)-3-hydroxypropyl]azetidin-2-one

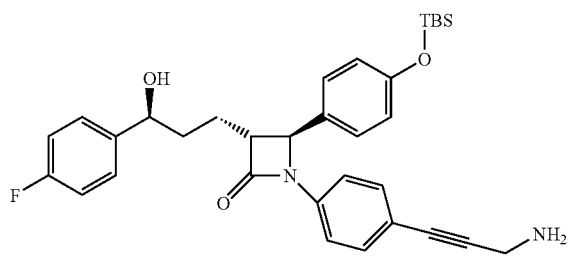

To a solution of 8 mg (0.013 mmol, 1 equiv.) (3R,4S)-4-(4-{[tert-butyl(dimethyl)silyl]oxy}phenyl)-3-[(3S)-3-(4-fluorophenyl)-3-hydroxypropyl]-1-(4-iodophenyl)azetidin-2-one (intermediate step A) in 0.5 mL DMF was added 2.2 mg (0.002 mmol, 0.15 equiv.) tetrakistriphenylphosphine palladium(0) and 0.8 mg (0.004 mmol, 0.3 equiv) copper(I) iodide. The solution was deoxygenated by a slow stream of anhydrous nitrogen delivered by a needle through a rubber septum. To the resulting solution was added by syringe 0.012 mL (0.177 mmol, 14 equiv.) propargyl amine and 0.012 mL (0.09 mmol, 7 equiv.) triethylamine. The resulting solution was stirred at room temperature for 1.25 hr at which time the solvent was removed under vacuum. The residue was purified by prep. Tlc eluting with $CH_2Cl_2$/MeOH (9/1) to afford the title compound. m/z (ES) 559.3 ($MH^+$), 542.3 ($MH-NH_3^+$).

Step C: Preparation of (3R,4S)-1-[4-(3-aminoprop-1-yn-1-yl)phenyl]-3-[(3S)-3-{[tert-butyl(dimethyl)silyl]oxy}-3-(4-fluorophenyl)propyl]-4-(4-{[tert-butyl(dimethyl)silyl]oxy}phenyl)azetidin-2-one

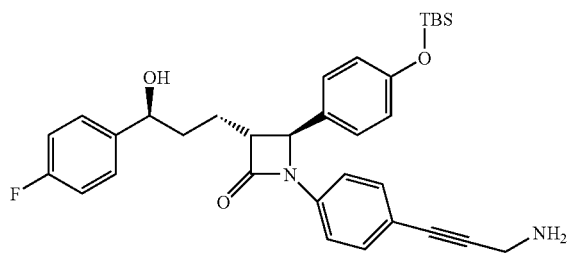

To a solution of 8 mg (0.014 mmol, 1 equiv) (3R,4S)-1-[4-(3-aminoprop-1-yn-1-yl)phenyl]-4-(4-{[tert-butyl(dimethyl)silyl]oxy}phenyl)-3-[(3S)-3-(4-fluorophenyl)-3-hydroxypropyl]azetidin-2-one (intermediate step B) in 1 mL anhydrous methylene chloride under inert atmosphere at room temperature was added 0.007 mL (0.057 mmol, 4 equivalents) 2,6-lutidine followed by 0.01 mL (0.043 mmol, 3 equiv.) tert-butyldimethylsilyl trifluoromethanesulfonate. The resulting reaction mixture was stirred for 15 minutes then quenched by the addition of 0.5 mL of sat. aq. solution of sodium bicarbonate. The resulting mixture was transferred to a separatory funnel, extracted with methylene chloride (2×5 mL). The combined organic extracts were dried over anhydrous $Na_2SO_4$ filtered and the solvent removed under vacuum. The residue was purified by prep. Tlc eluting with $CH_2Cl_2$/MeOH (95/5) to afford the title compound. m/z (ES) 674.4 ($M+H^+$), 656.4 ($MH-NH_3^+$), 541.4 ($MH-OTBS^+$).

Step D: Preparation of [$^{35}$S]propargylamine sulfonamide N-({4-[(2S,3R)-2-(4-{[tert-butyl(dimethyl)silyl]oxy}phenyl)-3-((3S)-3-{[tert-butyl(dimethyl)silyl]oxy}-3-phenylpropyl)-4-oxoazetidin-1-yl]phenyl}ethynyl)methanesulfonamide The appropriate volume of [$^{35}$S]methane sulfonyl chloride [1](see Dean, D. C.; et al., *J. Med. Chem.* 1996, 39, 1767)] totaling 145 mCi was removed from a stock solution in methylene chloride and placed in a 5 mL conical flask. It was then distilled at atmospheric pressure until the volume was approximately 25 μL. To this solution was immediately added a solution of 10 mg of (3R,4S)-1-[4-(3-aminoprop-1-yn-1-yl)phenyl]-3-[(3S)-3-{[tert-butyl(dimethyl)silyl]oxy}-3-(4-fluorophenyl)propyl]-4-(4-{[tert-butyl(dimethyl)silyl]oxy}phenyl)azetidin-2-one (intermediate step C) and 5 μL of triethylamine in 25 μL of methylene chloride. Stirred at room temperature for 30 minutes at which time it was concentrated to near dryness under a slow stream of nitrogen. This reaction mixture, which had a radiochemical purity of 41.4% by HPLC (Zorbax XDB C8 column, 4.6×150 mm, 50% acetonitrile in $H_2O$ (0.1% TFA) to 100% acetonitrile in 10 min, hold @ 100% acetonitrile for 5 min, 1 mL/min, $t_R$=12.9 min) was taken on directly to the next step.

Step E Preparation of [$^{35}$S] N-[(4-{(2S,3R)-2-(4-hydroxyphenyl)-3-[(3S)-3-phenylpropyl]-4-oxoazetidin-1-yl}phenyl)ethynyl]methanesulfonamide The crude reaction mixture containing [$^{35}$S]propargylamine sulfonamide N-({4-[(2S,3R)-2-(4-{[tert-butyl(dimethyl)silyl]oxy}phenyl)-3-((3S)-3-{[tert-butyl(dimethyl)silyl]oxy}-3-phenylpropyl)-4-oxoazetidin-1-yl]phenyl}ethynyl) methanesulfonamide (intermediate of step D) was treated with 100 μL of a premixed solution containing 95 μL of acetonitrile and 5 μL of 48% aq. HF and stirred at room temperature for six hours. It was then concentrated to near dryness under a slow stream of nitrogen, diluted with 10 mL of $H_2O$, passed through a 200 mg C8 solid phase extraction cartridge, and eluted with methanol. The methanol solution was concentrated under a slow stream of nitrogen and subjected to semi-preparative chromatography (Zorbax XDB C8 column, 9.4×250 mm, 25% acetonitrile in $H_2O$ (0.1% TFA) to 45% acetonitrile in 30 min, 4 ml/min, 1×0.5 mL injection). 23.6 mCi of product was obtained, which had a radiochemical purity of 99.6% by HPLC (Zorbax XDB C8 column, 4.6×150 mm, 5% acetonitrile in $H_2O$ (0.1% TFA) to 100% acetonitrile in 15 min, hold @ 100% acetonitrile for 5 min, 1 mL/min, $t_R$=10.4 min).

Step F Preparation of Compound [$^{35}$S] 7b

In a 12 mL scintillation vial was added 200 μL of 0.5 M Bis Tris Buffer pH=7.5, 200 μL of 0.1 M $MgCl_2$, 1.5 mL of $H_2O$, and 50 μL of dog liver microsomes. The mixture was agitated gently. To this mixture was added 8 μL of a 25 mg/mL solution of alamethicin in 1:1 acetonitrile:$H_2O$, 200 μL of 20 mM UDPGA, 200 μL of 0.1 M saccharic acid lactone, and 4 mCi of [$^{35}$S] N-[(4-{(2S,3R)-2-(4-hydroxyphenyl)-3-[(3S)-3-phenylpropyl]-4-oxoazetidin-1-yl}phenyl)ethynyl]methanesulfonamide in 50 μL of acetonitrile. The mixture was incubated at 37° C. for 2.5 hrs with shaking. It was then cooled to 0° C. and quenched with the addition of 3 mL of 1% formic acid in acetonitrile. This resulting slurry was centrifuged at 3000 rpm for 3 min. The supernate was removed from the protein pellet with a pipet. An additional 4 mL of acetonitrile was added to the pellet and the centrifugation was repeated. Both supernates were combined, diluted to a total volume of 40 mL with $H_2O$, passed through a 1 g STRATA X™ solid phase extraction cartridge, and eluted with methanol. The methanol solution was concentrated under a slow stream of nitrogen and subjected to semi-preparative chromatography (ZORBAX XDB™ C8 250×9.4 mm column, 30% acetonitrile in $H_2O$ (0.1% TFA), 4 mL/min, 1×200 μL injection). 1.4 mCi of product was obtained which had a radiochemical purity of 98.5% by HPLC ZORBAX XDB™ C8 column, 4.6×150 mm, 30% acetonitrile in $H_2O$ (0.1% TFA), 1 mL/min, $t_R$=10.4 min) and coeluted with an authentic sample of 7b. LC/MS m/z=508 (product—glucuronide —$H_2O$), SA=699 Ci/mmol.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I

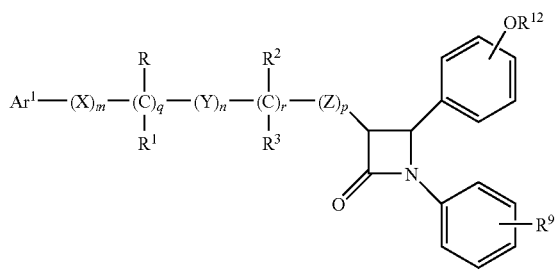

and the pharmaceutically acceptable salts and esters thereof, wherein $Ar^1$ is selected from the group consisting of aryl and $R^4$-substituted aryl;

X, Y and Z are independently selected from the group consisting of —$CH_2$—, —CH($C_{1-6}$alkyl)- and —C($C_{1-6}$alkyl)$_2$—;

R is selected from the group consisting of —$OR^6$, —O(OC)$R^6$, —O(OC)$OR^8$, —O(CO)$OR^9$, —O(CO)$NR^6R^7$, a sugar residue, a disugar residue, a trisugar residue and a tetrasugar residue;

$R^1$ is selected from the group consisting of —H, —$C_{1-6}$alkyl and aryl, or R and $R^1$ together are oxo;

$R^2$ is selected from the group consisting of —$OR^6$, —O(CO)$R^6$, —O(CO)$OR^8$, —O(CO)$OR^9$ and —O(CO)$NR^6R^7$;

$R^3$ is selected from the group consisting of —H, —$C_{1-6}$alkyl and aryl or $R^2$ and $R^3$ together are oxo;

q and r are integers each independently selected from 0 and 1;

t is an integer selected from 0, 1 and 2;

m, n and p are integers each independently selected from 0, 1, 2, 3 and 4;

$R^4$ is 1-5 substituents independently selected at each occurrence from the group consisting of:
—$OR^5$, —O(CO)$R^5$, —O(CO)$OR^8$, —O—$C_{1-5}$alkyl-$OR^5$, —O(CO)$NR^5R^6$, —$NR^5R^6$, —$NR^5$(CO)$R^6$, —$NR^5$(CO)$OR^8$, —$NR^5$(CO)$NR^6R^7$, —$NR^5SO_2R^8$, —$COOR^5$, —$CONR^5R^6$, —$COR^5$, —$SO_2NR^5R^6$, —$S(O)_tR^8$, —O—$C_{1-10}$alkyl-$COOR^5$, —O—$C_{1-10}$alkyl-$CONR^5R^6$ and fluoro;

$R^5$, $R^6$ and $R^7$ are independently selected at each occurrence from the group consisting of —H, $C_{1-6}$alkyl, aryl and aryl-substituted $C_{1-6}$alkyl;

$R^8$ is independently selected from the group consisting of $C_{1-6}$alkyl, aryl and aryl-substituted $C_{1-6}$alkyl;

$R^9$ is selected from the group consisting of —C≡C—$CH_2$—$NR^{10}R^{11}$, —C≡C—C(O)$R^{13}$, and —($CH_2$)$_3$—$NR^{10}R^{14}$;

$R^{10}$ is independently selected at each occurrence from —H and —$C_{1-3}$alkyl;

$R_{11}$ is selected from the group consisting of —H, —$C_{1-3}$alkyl, —C(O)—$C_{1-3}$alkyl, —C(O)—$NR^{10}R^{10}$, —$SO_2$—$C_{1-3}$alkyl, and —$SO_2$-phenyl;

$R^{12}$ is selected from the group consisting of:

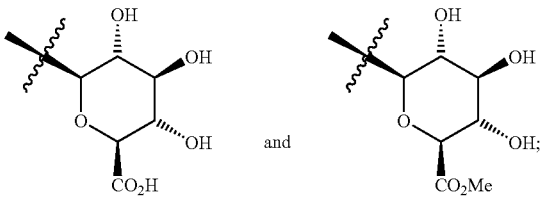

$R^{13}$ is selected from the group consisting of —OH and —$NR^{10}R^{11}$; and $R^{14}$ is selected from the group consisting of —C(O)—$C_{1-3}$alkyl, —C(O)—$NR^{10}R^{10}$, —$SO_2$—$C_{1-3}$alkyl and —$SO_2$-phenyl.

2. The compound of claim 1 wherein R is selected from the group consisting of —$OR^6$, —O(CO)$R^6$, —O(CO)$OR^9$, and —O(CO)$NR^6R^7$, a sugar residue, a disugar residue, a trisugar residue and a tetrasugar residue; $R^2$ is selected from the group consisting of —$OR^6$, —O(CO)$R^6$, —O(CO)$OR^9$ and —O(CO)$NR^6R^7$; and t is selected from 0 and 1.

3. The compound of claim 2 wherein m, n and p are each independently selected from 0, 1, 2, 3 and 4; at least one of q and r is 1 and the sum of m, n, p, q and r is 1, 2, 3, 4, 5 or 6; and provided that when p is 0 and r is 1, the sum of m, q and n is 1, 2, 3, 4, or 5.

4. The compound of claim 1 wherein at least one of q and r is 1, and the sum of m, n, p, q and r is 1, 2, 3, 4, 5 or 6.

5. The compound of claim 1 wherein R is selected from the group consisting of —$OR^6$, —O(CO)$R^6$, —O(CO)$OR^8$, —O(CO)$NR^6R^7$, a sugar residue, a disugar residue, a trisugar residue and a tetrasugar residue; and $R^2$ is selected from the group consisting of —$OR^6$, —O(CO)$R^6$, —O(CO)$OR^8$ and —O(CO)$NR^6R^7$.

6. The compound of claim 5 wherein at least one of q and r is 1, and the sum of m, n, p, q and r is 1, 2, 3, 4, 5 or 6.

7. The compound of claim 1 of Formula Ia:

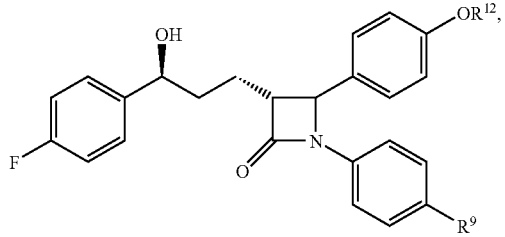

and the pharmaceutically acceptable salts and esters thereof.

8. The compound of claim 1 wherein $R^9$ is —C≡C—$CH_2$—$NR^{10}R^{11}$.

9. The compound of claim 3 wherein $R^9$ is —C≡C—$CH_2$—$NR^{10}R^{11}$.

10. The compound of claim 6 wherein $R^9$ is —C≡C—$CH_2$—$NR^{10}R^{11}$.

11. The compound of claim 7 selected from the group consisting of:

| Compound | $R^{12}$ | $R^9$ |
|---|---|---|
| 7a) | methyl ester glucuronide | (propargyl-NHSO₂Me) |
| 7b) | glucuronide | (propargyl-NHSO₂Me) |
| 7c) | methyl ester glucuronide | (propargyl-NH₂) |
| 7d) | glucuronide | (propargyl-NH₂) |
| 7e) | methyl ester glucuronide | (propargyl-NHC(O)Me) |
| 7f) | glucuronide | (propargyl-NHC(O)Me) |
| 7g) | methyl ester glucuronide | (propargyl-N(Me)SO₂Me) |
| 7h) | glucuronide | (propargyl-N(Me)SO₂Me) |
| 7i) | methyl ester glucuronide | (propargyl-NHSO₂Ph) |
| 7j) | glucuronide | (propargyl-NHSO₂Ph) |
| 7k) | methyl ester glucuronide | (propargyl-NHC(O)N(Me)Me) |
| 7l) | glucuronide | (propargyl-NHC(O)N(Me)Me) |
| 7m) | methyl ester glucuronide | (propargyl-N(Me)Me) |
| 7n) | glucuronide | (propargyl-N(Me)Me) |
| 8b) | glucuronide | —C≡CH |
| 9a) | glucuronide | —$(CH_2)_3$—$NHSO_2CH_3$ |
| 9b) | glucuronide | —$(CH_2)_3$—$NHSO_2CH_3$ |
| 10e) | glucuronide | —C≡C—COOH |
| 11b) | glucuronide | —C≡C—C(O)NHCH₂CH₃ | and the pharmaceutically acceptable salts and esters thereof.

12. A method of reducing plasma cholesterol levels comprising administering a therapeutically effective amount of a compound of claim 1 to a patient in need of such treatment.

13. The method of claim 12 comprising administering a therapeutically effective amount of the compound in combination with a therapeutically effective amount of a cholesterol biosynthesis inhibitor to a patient in need of such treatment.

14. The method of claim 13 wherein the cholesterol biosynthesis inhibitor is an HMG-CoA reductase inhibitor.

15. A method of treating hypercholesterolemia comprising administering a therapeutically effective amount of a compound of claim 1 to a patient in need of such treatment.

16. A method of treating atherosclerosis comprising administering a therapeutically effective amount of a compound of claim 1 to a patient in need of such treatment.

17. A method of reducing the risk for having an atherosclerotic disease event comprising administering a prophylactically effective amount of a compound of claim 1 to a patient in at risk for such an event.

18. A pharmaceutical composition comprising a compound of claim 1 and a pharmaceutically acceptable carrier.

19. The pharmaceutical composition of claim 18 additionally comprising a cholesterol biosynthesis inhibitor.

20. The pharmaceutical composition of claim 19 wherein the cholesterol biosynthesis inhibitor is an HMG-CoA reductase inhibitor.

21. The compound of claim 11 selected from the group consisting of:
4-[(2S,3R)-3-[(3S)-3-(4-fluorophenyl)-3-hydroxypropyl]-1-(4-{3-[(methylsulfonyl)amino]propyl}phenyl)-4-oxoazetidin-2-yl]phenyl methyl β-D-glucopyranosiduronate; 4-[(2S,3R)-3-[(3S)-3-(4-fluorophenyl)-3-hydroxypropyl]-1-(4-{3-[(methylsulfonyl)amino]propyl}phenyl)-4-oxoazetidin-2-yl]phenyl β-D-glucopyranosiduronic acid; and the pharmaceutically acceptable salts and esters thereof.

22. The compound of claim 11 selected from the group consisting of:
4-[(2S,3R)-3-[(3S)-3-(4-fluorophenyl)-3-hydroxypropyl]-1-(4-{3-[(methylsulfonyl)amino]prop-1-yn-1-yl}phenyl)-4-oxoazetidin-2-yl]phenyl methyl β-D-glucopyranosiduronate;
4-[(2S,3R)-3-[(3S)-3-(4-fluorophenyl)-3-hydroxypropyl]-1-(4-{3-[(methylsulfonyl)amino]prop-1-yn-1-yl}phenyl)-4-oxoazetidin-2-yl]phenyl β-D-glucopyranosiduronic acid; and the pharmaceutically acceptable salts and esters thereof.

23. The compound of claim 22 selected from the group consisting of:
[$^{35}$S]4-[(2S,3R)-3-[(3S)-3-(4-fluorophenyl)-3-hydroxypropyl]-1-(4-{3-[(methylsulfonyl)amino]prop-1-yn-1-yl}phenyl)-4-oxoazetidin-2-yl]phenyl methyl β-D-glucopyranosiduronate; [$^{35}$S]4-[(2S,3R)-3-[(3S)-3-(4-fluorophenyl)-3-hydroxypropyl]-1-(4-{3-[(methylsulfonyl)amino]prop-1-yn-1-yl}phenyl)-4-oxoazetidin-2-yl]phenyl β-D-glucopyranosiduronate; and the pharmaceutically acceptable salts and esters thereof.

24. The compound of claim 1 wherein:
R9 is selected from the group consisting of —C≡C—CH$_2$—NR$^{10}$R$^{11}$, —C≡C—C(O)R$^{13}$ wherein R$^{13}$ is —NR$^{10}$R$^{11}$, and —(CH$_2$)$_3$—NR$^{10}$R$^{14}$;

R$^{11}$ is selected from the group consisting of —$^{35}$SO$_2$—C$_{1-3}$ alkyl, and —$^{35}$SO$_2$-phenyl; and
R$^{14}$ is selected from the group consisting —$^{35}$SO$_2$—C$_{1-3}$ alkyl and —$^{35}$S$^2$-phenyl;
and the pharmaceutically acceptable salts and esters thereof.

25. The compound of claim 1 having the structural formula

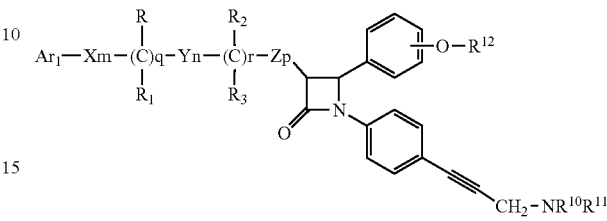

wherein R$^{12}$ is selected from the group consisting of

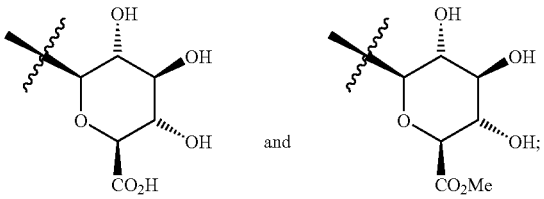

and the pharmaceutically acceptable salts and esters thereof.

26. The compound of claim 25 wherein R$^{11}$ is selected from the group consisting of —$^{35}$SO$_2$—C$_{1-3}$alkyl and —$^{35}$SO$_2$-phenyl; and the pharmaceutically acceptable salts and esters thereof.

27. The compound of claim 7 wherein R$^9$ is —C≡C—CH$_2$—NR$^{10}$R$^{11}$, and the pharmaceutically acceptable salts and esters thereof.

28. The compound of claim 4 wherein R$^9$ is —C≡C—CH$_2$—NR$^{10}$R$^{11}$, and the pharmaceutically acceptable salts and esters thereof.

29. The compound of claim 7 wherein:
R$^9$ is selected from the group consisting of —C≡C—CH$_2$—NR$^{10}$R$^{11}$, —C≡C—C(O)R$^{13}$ wherein R$^{13}$ is —NR$^{10}$R$^{11}$, and —(CH$_2$)$_3$-NR$^{10}$R$^{14}$;
R$^{11}$ is selected from the group consisting of —$^{35}$SO$_2$—C$_{1-3}$ alkyl and —$^{35}$SO$_2$-phenyl; and
R$^{14}$ is selected from the group consisting of —$^{35}$SO$_2$—C$_{1-3}$ alkyl and —$^{35}$SO$_2$-phenyl;
and the pharmaceutically acceptable salts and esters thereof.

* * * * *